US012329784B2

(12) United States Patent
Li et al.

(10) Patent No.: US 12,329,784 B2
(45) Date of Patent: Jun. 17, 2025

(54) GUT MICROBIOTA AND TREATMENT OF CANCER

(71) Applicants: Sanford Burnham Prebys Medical Discovery Institute, La Jolla, CA (US); Technion Research & Development Foundation Ltd., Haifa (IL)

(72) Inventors: Yan Li, La Jolla, CA (US); Scott Peterson, La Jolla, CA (US); Linda Bradley, La Jolla, CA (US); Roberto Tinoco, La Jolla, CA (US); Ze'ev Ronai, San Diego, CA (US); Shiri Ashkenazi, Haifa (IL)

(73) Assignees: Sanford Burnham Prebys Medical Discovery Institute, La Jolla, CA (US); Technion Research & Development Foundation Ltd., Haifa (IL)

( * ) Notice: Subject to any disclaimer, the term of this patent is extended or adjusted under 35 U.S.C. 154(b) by 165 days.

(21) Appl. No.: 18/103,166

(22) Filed: Jan. 30, 2023

(65) Prior Publication Data
US 2023/0270795 A1   Aug. 31, 2023

Related U.S. Application Data

(63) Continuation of application No. 16/461,850, filed as application No. PCT/US2017/062257 on Nov. 17, 2017, now Pat. No. 11,571,446.

(60) Provisional application No. 62/436,206, filed on Dec. 19, 2016, provisional application No. 62/424,237, filed on Nov. 18, 2016.

(51) Int. Cl.
| A61K 35/74 | (2015.01) |
| A61K 31/7004 | (2006.01) |
| A61K 31/7008 | (2006.01) |
| A61K 31/7024 | (2006.01) |
| A61K 31/733 | (2006.01) |
| A61K 39/395 | (2006.01) |
| A61P 35/00 | (2006.01) |
| C07K 16/28 | (2006.01) |

(52) U.S. Cl.
CPC .......... *A61K 35/74* (2013.01); *A61K 31/7004* (2013.01); *A61K 31/7008* (2013.01); *A61K 31/7024* (2013.01); *A61K 31/733* (2013.01); *A61K 39/3955* (2013.01); *A61P 35/00* (2018.01); *C07K 16/2818* (2013.01)

(58) Field of Classification Search
None
See application file for complete search history.

(56) References Cited

U.S. PATENT DOCUMENTS

| 7,785,635 | B1 | 8/2010 | Boileau et al. | |
| 11,571,446 | B2 * | 2/2023 | Li | ........................ A61K 31/166 |
| 2002/0142047 | A1 | 10/2002 | Johnson et al. | |
| 2015/0225692 | A1 | 8/2015 | Bhatia et al. | |
| 2016/0106824 | A1 | 4/2016 | Palena et al. | |
| 2016/0193257 | A1 * | 7/2016 | Honda | .................. A61K 35/747 424/93.4 |
| 2016/0193258 | A1 | 7/2016 | Berry et al. | |
| 2019/0365829 | A1 | 12/2019 | Li et al. | |
| 2020/0129569 | A1 * | 4/2020 | Wargo | ..................... A61P 35/00 |

FOREIGN PATENT DOCUMENTS

| WO | WO 2015/037000 | 3/2015 |
| WO | WO 2019/023555 | 1/2019 |

OTHER PUBLICATIONS

Li et al. 2016 (Probiotics modulated gut microbiota suppresses hepatocellular carcinoma growth in mice; PNAS E1306-E1315), (Year: 2016).*
Peterson et al. 2014 (Immune homeostasis, dysbiosis and therapeutic modulation of gut microbiota; Clinical & Experimental Immunology 179: 363-377) (Year: 2014).*
Botticelli et al., "Cross-talk between microbiota and immune fitness to steer and control response to anti PD-1/PDL-1 treatment," ONCOTARGET, Oct. 2016, 8(5):8890-8899.
Bultnnan, "Emerging roles of the microbiome in cancer," Carcinogenesis, Feb. 2014, 35(2):249-255.
Elinav et al., "Inflammation-induced cancer: crosstalk between tumours, immune cells and microorganisms," Nature Reviews Cancer, Nov. 2013, 13(11):759-71.
EP Office Action in European Appln. No. 17818347, dated Jul. 9, 2021, 16 pages.
Flaherty et al., "Combined BRAF and MEK inhibition in Melanoma with BRAF V600 mutations," N Engl J Med., Nov. 2012, 367(18):1694-1703.
Hu-Lieskovan et al., "Improved antitumor activity of immunotherapy with BRAF and MEK inhibitors in BRAFV600E melanoma," Science Translational Medicine, 2015, 7(279):1-13.
Jakob et al., "NRAS mutation status is an independent prognostic factor in metastatic melanoma," Cancer, Aug. 2012, 118(16):4014-4023.

(Continued)

Primary Examiner — Mary Maille Lyons
(74) Attorney, Agent, or Firm — Fish & Richardson P.C.

(57) ABSTRACT

The ubiquitin ligase, RNF5, regulates the gut microbiota composition and influences the immune checkpoint response to tumors. RNF5 deficient animals exhibit significant inhibition of tumor development as well as an altered gut microbiota composition. Methods of treating cancer by administering to a subject one or more selected bacterial species and/or one or more prebiotics that promote the growth of one or more selected bacterial species are disclosed. Also disclosed are methods of treating cancer by administering to a subject one or more selected bacterial species and/or one or more prebiotics that promote the growth of one or more selected bacterial species in combination with one or more anti-cancer agents.

15 Claims, 20 Drawing Sheets

(56) References Cited

OTHER PUBLICATIONS

Johnson et al., "Impact of NRAS mutations for patients with advanced melanoma treated with immune therapies," Cancer Immunology Research, Mar. 2015, 3(3):288-295.

Li et al., "Gut microbiota dependent anti-tumor immunity restricts melanoma growth in Rnf5-/- mice," Nature Communications, 2019, 10:1492, 16 pages.

Li et al., "Probiotics modulated gut microbiota suppresses hepatocellular carcinoma growth in mice," Proceedings National Academy of Sciences PNAS, Feb. 2016, 113(9):E1306-E1315.

McDermott et al., "Malignant Melanoma Metastatic to the Gastrointestinal Tract," AJR, Apr. 1996, 166(4):809-813.

Medenna et al., "Checkpoint control and cancer," Oncogene, May 2012, 31(21):2601-2613.

Palucka et al., "The Basis of Oncoimmunology," Cell, Mar. 2016, 164:1233-1247.

PCT International Preliminary Report on Patentability in International No. PCT/US2017/062257, dated May 21, 2019, 15 pages.

PCT International Search Report and Written Opinion in International Application No. PCT/US2017/062257, dated Feb. 26, 2018, 22 pages.

Peterson et al., "Immune homeostasis, dysbiosis and therapeutic modulation of gut microbiota," Clinical & Experimental Immunology, 2014, 179:363-377.

Reddy et al., "Influences of BRAF Inhibitors on the Immune Microenvironment and the Rationale for Combined Molecular and Immune Targeted Therapy," Current Oncology Reports, May 2016, 18:42, 9 pages.

Sharma et al., "Immune Checkpoint Targeting in Cancer Therapy: Toward Combination Strategies With Curative Potential," Cell, Apr. 2015, 161:205-14.

Stofilova et al., "Co-administration of a probiotic strain Lactobacillus plantarum LS/07 CCM776 with prebiotic inulin alleviates the intestinal inflammation in rats exposed to N,N-dinnethylhyrazine, "International Immunopharmacology, Feb. 2015, 24(2):361-368.

Taper et al., "Possible Adjuvant Cancer Therapy by Two Prebiotics—Insulin or oligofructose," In Vivo, Jan. 2005, 19(1):201-204.

Vetizou et al., "Anticancer immunotherapy by CTLA-4 blockade relies on the gut microbiota," Science, Nov. 2015, 350(6264):1079-1084.

Yan et al., "Prebiotic-Induced Anti-tumor Immunity Attenuates Tumor Growth," Cell Reports, Feb. 1, 2020, 30(6):1753-1766.

Brown et al., "The use of vemurafenib in Australian patients with unresectable or metastatic melanoma containing the V600 BRAF gene mutation," Asia-Pacific Journal of Clinical Oncology, Apr. 10, 2014, 10(Suppl. 3):1-15.

\* cited by examiner

| | Metabolite Name | Formula | WT needed amount | KO needed amount |
|---|---|---|---|---|
| Mucin | Galactose | $C_6H_{12}O_6$ | 10 | 40 |
| Mucin | N-Acetyl-D-glucosamine | $C_8H_{15}NO_6$ | 20 | 50 |
| Mucin | N-Acetyl-D-mannosamine | $C_8H_{15}NO_6$ | 40 | 30 |
| Inulin | Glucose-1-phosphate | $C_6H_{13}O_9P$ | 20 | 50 |
| Inulin | D-Fructose | $C_6H_{12}O_6$ | 20 | 30 |

Fig. 4C

GUT MICROBIOTA AND TREATMENT OF CANCER

CROSS-REFERENCE TO RELATED APPLICATIONS

This application is a continuation of U.S. application Ser. No. 16/461,850, filed May 17, 2019, which is a 371 U.S. National Phase Application of Application No. PCT/US2017/062257, filed Nov. 17, 2017, which claims the benefit of priority to U.S. Provisional Application No. 62/424,237, filed Nov. 18, 2016, and U.S. Provisional Application No. 62/436,206, filed Dec. 19, 2016, the contents of which are incorporated by reference in their entirety herein.

STATEMENT OF FEDERALLY SPONSORED RESEARCH

This invention was made with government support under R35 CA197465 awarded by the National Institutes of Health (NIH) and W81XWH-16-1-0517 awarded by the Department of Defense (DoD). The government has certain rights in the invention.

BACKGROUND

The clinical efficacy of immune checkpoint inhibitors in several cancer types has demonstrated the importance of targeting this regulatory axis for cancer treatment (Sharma et al. (2015) Cell 161:205-14). However, most of the successes have been obtained with inhibitors that target only a few immune checkpoint receptors and ligands and are effective in a subset of tumor types (Palucka et al. (2016) Cell 164:1233-47). Thus, a greater understanding of the mechanisms underlying the selectivity of the tumor response, the control of immune checkpoint components, and the emergence of tumors resistant to this therapy is needed (Reddy et al. (2016) Current Oncology Reports 18:42).

SUMMARY

The invention is based, at least in part, on the discovery of an unexpected role for the ubiquitin ligase, RNF5, in regulating the gut microbiota composition and influencing the immune checkpoint response to tumors. RNF5 deficient animals exhibited significant inhibition of tumor development combined with an altered gut microbiota composition. Treatment of wild-type animals with selected prebiotics resulted in inhibition of tumor growth and an altered gut microbiota similar to that observed in RNF5 deficient animals.

In one aspect, the disclosure features a method of treating a cancer in a human subject in need thereof by administering to the human subject a composition comprising a therapeutically effective amount of one or more bacteria selected from the group consisting of *Oscillibacter valericigenes, Acetatifactor muris, Alistipes putredinis, Alistipes finegoldii, Clostridium clostridioforme, Lactobacillus animalis, Lactobacillus murinus, Bacteroides massiliensis, Bacteroides sartorii, Muribaculum intestinale, Parasutterella excrementihominis, Clostridium methylpentosum,* and *Bacteroides rodentium.*

In another aspect, the disclosure features a method of treating a cancer in a human subject in need thereof by administering to the human subject a composition comprising a therapeutically effective amount of one or more bacteria selected from the group consisting of *Bacteroides acidifaciens, Bacteroides xylanisolvens, Bacteroides chinchilla (B. sartorii), B. thetaiotaomicron, B. fragilis, Dysgonomonas wimpennyi, Parabacteroides merdae, Flavobacterium, Staphylococcus* spp., *Staphylococcus sciuri, Staphylococcus xylosus, Helicobacter ganmani, Helicobacter hepaticus, Enterobacter hormaechei, Porphyromonas canis, Porphyromonas gingivicanis, Rickenella microfusus, Olivibacter* spp, *P. goldsteinii, P. koreensis, Pedobacter* spp., *O. sinus, Blautia hansenii,* and *Lachnospira pectinoschiza.*

Also disclosed is the use of one or more bacteria selected from the group consisting of *Oscillibacter valericigenes, Acetatifactor muris, Alistipes putredinis, Alistipes finegoldii, Clostridium clostridioforme, Lactobacillus animalis, Lactobacillus murinus, Bacteroides massiliensis, Bacteroides sartorii, Muribaculum intestinale, Parasutterella excrementihominis, Clostridium methylpentosum,* and *Bacteroides rodentium* for the preparation of a medicament for treatment of a cancer in a human subject.

Also disclosed is the use of one or more bacteria selected from the group consisting of *Bacteroides acidifaciens, Bacteroides xylanisolvens, Bacteroides chinchilla (B. sartorii), B. thetaiotaomicron, B. fragilis, Dysgonomonas wimpennyi, Parabacteroides merdae, Flavobacterium, Staphylococcus* spp., *Staphylococcus sciuri, Staphylococcus xylosus, Helicobacter ganmani, Helicobacter hepaticus, Enterobacter hormaechei, Porphyromonas canis, Porphyromonas gingivicanis, Rickenella microfusus, Olivibacter* spp, *P. goldsteinii, P. koreensis, Pedobacter* spp., *O. sinus, Blautia hansenii,* and *Lachnospira pectinoschiza* for the preparation of a medicament for treatment of a cancer in a human subject.

Also disclosed is a composition comprising a therapeutically effective amount of one or more bacteria selected from the group consisting of *Oscillibacter valericigenes, Acetatifactor muris, Alistipes putredinis, Alistipes finegoldii, Clostridium clostridioforme, Lactobacillus animalis, Lactobacillus murinus, Bacteroides massiliensis, Bacteroides sartorii, Muribaculum intestinale, Parasutterella excrementihominis, Clostridium methylpentosum,* and *Bacteroides rodentium* for use in treatment of a cancer in a human subject.

Also disclosed is a composition comprising a therapeutically effective amount of one or more bacteria selected from the group consisting of *Bacteroides acidifaciens, Bacteroides xylanisolvens, Bacteroides chinchilla (B. sartorii), B. thetaiotaomicron, B. fragilis, Dysgonomonas wimpennyi, Parabacteroides merdae, Flavobacterium, Staphylococcus* spp., *Staphylococcus sciuri, Staphylococcus xylosus, Helicobacter ganmani, Helicobacter hepaticus, Enterobacter hormaechei, Porphyromonas canis, Porphyromonas gingivicanis, Rickenella microfusus, Olivibacter* spp, *P. goldsteinii, P. koreensis, Pedobacter* spp., *O. sinus, Blautia hansenii,* and *Lachnospira pectinoschiza* for use in treatment of a cancer in a human subject.

In another aspect, the disclosure features a method of treating a cancer in a human subject in need thereof by administering to the human subject a composition comprising a therapeutically effective amount of one or more prebiotics that promote the growth of one or more bacteria selected from the group consisting of *Oscillibacter valericigenes, Acetatifactor muris, Alistipes putredinis, Alistipes finegoldii, Clostridium clostridioforme, Lactobacillus animalis, Lactobacillus murinus, Bacteroides massiliensis, Bacteroides sartorii, Muribaculum intestinale, Parasutterella excrementihominis, Clostridium methylpentosum,* and *Bacteroides rodentium.*

In another aspect, the disclosure features a method of treating a cancer in a human subject in need thereof by administering to the human subject a composition comprising a therapeutically effective amount of one or more prebiotics that promote the growth of one or more bacteria selected from the group consisting of *Bacteroides acidifaciens, Bacteroides xylanisolvens, Bacteroides chinchilla (B. sartorii), B. thetaiotaomicron, B. fragilis, Dysgonomonas wimpennyi, Parabacteroides merdae, Flavobacterium, Staphylococcus* spp., *Staphylococcus sciuri, Staphylococcus xylosus, Helicobacter ganmani, Helicobacter hepaticus, Enterobacter hormaechei, Porphyromonas canis, Porphyromonas gingivicanis, Rickenella microfusus, Olivibacter* spp, *P. goldsteinii, P. koreensis, Pedobacter* spp., *O. sinus, Blautia hansenii,* and *Lachnospira pectinoschiza*.

Also disclosed is the use of one or more prebiotics that promote the growth of one or more bacteria selected from the group consisting of *Oscillibacter valericigenes, Acetatifactor muris, Alistipes putredinis, Alistipes finegoldii, Clostridium clostridioforme, Lactobacillus animalis, Lactobacillus murinus, Bacteroides massiliensis, Bacteroides sartorii, Muribaculum intestinale, Parasutterella excrementihominis, Clostridium methylpentosum,* and *Bacteroides rodentium* for the preparation of a medicament for treatment of a cancer in a human subject.

Also disclosed is the use of one or more prebiotics that promote the growth of one or more bacteria selected from the group consisting of *Bacteroides acidifaciens, Bacteroides xylanisolvens, Bacteroides chinchilla (B. sartorii), B. thetaiotaomicron, B. fragilis, Dysgonomonas wimpennyi, Parabacteroides merdae, Flavobacterium, Staphylococcus* spp., *Staphylococcus sciuri, Staphylococcus xylosus, Helicobacter ganmani, Helicobacter hepaticus, Enterobacter hormaechei, Porphyromonas canis, Porphyromonas gingivicanis, Rickenella microfusus, Olivibacter* spp, *P. goldsteinii, P. koreensis, Pedobacter* spp., *O. sinus, Blautia hansenii,* and *Lachnospira pectinoschiza* for the preparation of a medicament for treatment of a cancer in a human subject.

Also disclosed is a composition comprising a therapeutically effective amount of one or more prebiotics that promote the growth of one or more bacteria selected from the group consisting of *Oscillibacter valericigenes, Acetatifactor muris, Alistipes putredinis, Alistipes finegoldii, Clostridium clostridioforme, Lactobacillus animalis, Lactobacillus murinus, Bacteroides massiliensis, Bacteroides sartorii, Muribaculum intestinale, Parasutterella excrementihominis, Clostridium methylpentosum,* and *Bacteroides rodentium* for use in treatment of a cancer in a human subject.

Also disclosed is a composition comprising a therapeutically effective amount of one or more prebiotics that promote the growth of one or more bacteria selected from the group consisting of *Bacteroides acidifaciens, Bacteroides xylanisolvens, Bacteroides chinchilla (B. sartorii), B. thetaiotaomicron, B. fragilis, Dysgonomonas wimpennyi, Parabacteroides merdae, Flavobacterium, Staphylococcus* spp., *Staphylococcus sciuri, Staphylococcus xylosus, Helicobacter ganmani, Helicobacter hepaticus, Enterobacter hormaechei, Porphyromonas canis, Porphyromonas gingivicanis, Rickenella microfusus, Olivibacter* spp, *P. goldsteinii, P. koreensis, Pedobacter* spp., *O. sinus, Blautia hansenii,* and *Lachnospira pectinoschiza* for use in treatment of a cancer in a human subject.

In another aspect, the disclosure features a method of treating a cancer in a human subject in need thereof by administering to the human subject in combination: (1) a therapeutically effective amount of one or more bacteria selected from the group consisting of *Oscillibacter valericigenes, Acetatifactor muris, Alistipes putredinis, Alistipes finegoldii, Clostridium clostridioforme, Lactobacillus animalis, Lactobacillus murinus, Bacteroides massiliensis, Bacteroides sartorii, Muribaculum intestinale, Parasutterella excrementihominis, Clostridium methylpentosum,* and *Bacteroides rodentium*; and (2) a therapeutically effective amount of one or more prebiotics that promote the growth of one or more bacteria selected from the group consisting of *Oscillibacter valericigenes, Acetatifactor muris, Alistipes putredinis, Alistipes finegoldii, Clostridium clostridioforme, Lactobacillus animalis, Lactobacillus murinus, Bacteroides massiliensis, Bacteroides sartorii, Muribaculum intestinale, Parasutterella excrementihominis, Clostridium methylpentosum,* and *Bacteroides rodentium*.

In another aspect, the disclosure features a method of treating a cancer in a human subject in need thereof by administering to the human subject in combination: (1) a therapeutically effective amount of one or more bacteria selected from the group consisting of *Bacteroides acidifaciens, Bacteroides xylanisolvens, Bacteroides chinchilla (B. sartorii), B. thetaiotaomicron, B. fragilis, Dysgonomonas wimpennyi, Parabacteroides merdae, Flavobacterium, Staphylococcus* spp., *Staphylococcus sciuri, Staphylococcus xylosus, Helicobacter ganmani, Helicobacter hepaticus, Enterobacter hormaechei, Porphyromonas canis, Porphyromonas gingivicanis, Rickenella microfusus, Olivibacter* spp, *P. goldsteinii, P. koreensis, Pedobacter* spp., *O. sinus, Blautia hansenii,* and *Lachnospira pectinoschiza*; and (2) a therapeutically effective amount of one or more prebiotics that promote the growth of one or more bacteria selected from the group consisting of *Bacteroides acidifaciens, Bacteroides xylanisolvens, Bacteroides chinchilla (B. sartorii), B. thetaiotaomicron, B. fragilis, Dysgonomonas wimpennyi, Parabacteroides merdae, Flavobacterium, Staphylococcus* spp., *Staphylococcus sciuri, Staphylococcus xylosus, Helicobacter ganmani, Helicobacter hepaticus, Enterobacter hormaechei, Porphyromonas canis, Porphyromonas gingivicanis, Rickenella microfusus, Olivibacter* spp, *P. goldsteinii, P. koreensis, Pedobacter* spp., *O. sinus, Blautia hansenii,* and *Lachnospira pectinoschiza*.

Also disclosed is the combination of (1) a therapeutically effective amount of one or more bacteria selected from the group consisting of *Oscillibacter valericigenes, Acetatifactor muris, Alistipes putredinis, Alistipes finegoldii, Clostridium clostridioforme, Lactobacillus animalis, Lactobacillus murinus, Bacteroides massiliensis, Bacteroides sartorii, Muribaculum intestinale, Parasutterella excrementihominis, Clostridium methylpentosum,* and *Bacteroides rodentium*; and (2) a therapeutically effective amount of one or more prebiotics that promote the growth of one or more bacteria selected from the group consisting of *Oscillibacter valericigenes, Acetatifactor muris, Alistipes putredinis, murinus, Bacteroides massiliensis, Bacteroides sartorii, Muribaculum intestinale, Parasutterella excrementihominis, Clostridium methylpentosum,* and *Bacteroides rodentium* for simultaneous, separate, or sequential administration to a human subject for treatment of a cancer.

Also disclosed is the combination of (1) a therapeutically effective amount of one or more bacteria selected from the group consisting of *Bacteroides acidifaciens, Bacteroides xylanisolvens, Bacteroides chinchilla (B. sartorii), B. thetaiotaomicron, B. fragilis, Dysgonomonas wimpennyi, Parabacteroides merdae, Flavobacterium, Staphylococcus* spp., *Staphylococcus sciuri, Staphylococcus xylosus, Helicobacter ganmani, Helicobacter hepaticus, Enterobacter* hormaechei, Porphyromonas canis, Porphyromonas gingivicanis, Rickenella microfusus, Olivibacter spp, *P. goldsteinii*, *P. koreensis*, Pedobacter spp., *O. sinus*, *Blautia hansenii*, and *Lachnospira pectinoschiza*; and (2) a therapeutically effective amount of one or more prebiotics that promote the growth of one or more bacteria selected from the group consisting of *Bacteroides acidifaciens*, *Bacteroides xylanisolvens*, *Bacteroides chinchilla* (*B. sartorii*), *B. thetaiotaomicron*, *B. fragilis*, *Dysgonomonas wimpennyi*, *Parabacteroides merdae*, *Flavobacterium*, *Staphylococcus* spp., *Staphylococcus sciuri*, *Staphylococcus xylosus*, *Helicobacter ganmani*, *Helicobacter hepaticus*, *Enterobacter hormaechei*, *Porphyromonas canis*, *Porphyromonas gingivicanis*, *Rickenella microfusus*, *Olivibacter* spp, *P. goldsteinii*, *P. koreensis*, *Pedobacter* spp., *O. sinus*, *Blautia hansenii*, and *Lachnospira pectinoschiza* for simultaneous, separate, or sequential administration to a human subject for treatment of a cancer.

In some embodiments of the foregoing aspects, the one or more prebiotics are selected from the group consisting of a mucin, inulin, N-acetyl-D-glucosamine, N-acetyl-D-mannosamine, glucose-1-phosphate, D-fructose, a galactomannan, N-acetyl mannosamine, N-acetylgalactosamine, N-acetylneuraminic acid, N-acetyl glucosamine, galactose, fucose, mannose, human milk oligosaccharides, guar gum, dextrin, α-cellulose, β-D glucan, pectin, corn starch, and potato starch.

In some embodiments of the foregoing aspects, the one or more prebiotics includes porcine gastric mucin.

In some embodiments of the foregoing aspects, the one or more prebiotics includes N-acetyl-D-glucosamine and N-acetyl-D-mannosamine.

In some embodiments of the foregoing aspects, the one or more prebiotics includes glucose-1-phosphate and D-fructose.

Some embodiments of the foregoing aspects further include administering to the human subject one or more anti-cancer agents.

In some embodiments, the one or more anti-cancer agents comprises an immune checkpoint regulator. In one example, the immune checkpoint regulator is a checkpoint activator. An example of a checkpoint activator includes an agonist of costimulation by CD27, CD40, OX40, GITR, CD137, CD28, or ICOS (e.g., an agonist antibody that binds to CD27, CD40, OX40, GITR, CD137, CD28, or ICOS). In one example, the immune checkpoint regulator is a checkpoint inhibitor. An example of a checkpoint inhibitor includes an antagonist of PD-1, PD-L1, CTLA-4, A2AR, B7-H3, B7-H4, BTLA, IDO, KIR, LAG3, TIM-3, VISTA, CD160, TIGIT or PSGL-1 (e.g., an antagonist antibody that binds to PD-1, PD-L1, CTLA-4, A2AR, B7-H3, B7-H4, BTLA, IDO, KIR, LAG3, TIM-3, VISTA, CD160, TIGIT or PSGL-1). In one example, the immune checkpoint regulator is CDX-1127, TGN1412, NKTR-214, MEDI0562, MEDI6469, MEDI6383, JTX-2011, Keytruda (pembrolizumab), Opdivo (nivolumab), Yervoy (ipilimumab), tremelimumab, Tecentriq (atezolizumab), MGA271, indoximod, Epacadostat, lirilumab, BMS-986016, MPDL3280A, avelumab, durvalumab, MEDI4736, MEDI4737, TRX518, MK-4166, urelumab (BMS-663513), or PF-05082566 (PF-2566).

In some embodiments, the one or more anti-cancer agents comprises a BRAF inhibitor, such as vemurafenib or dabrafenib.

In some embodiments, the one or more anti-cancer agents comprises a MEK inhibitor, such as trametinib, cobimetinib, binimetinib, selumetinib, PD-325901, CI-1040, or TAK-733.

In some embodiments, the one or more anti-cancer agents comprises a BRAF inhibitor and a MEK inhibitor, such as (1) vemurafenib or dabrafenib, and (2) trametinib, cobimetinib, binimetinib, selumetinib, PD-325901, CI-1040, or TAK-733.

In some embodiments wherein a BRAF inhibitor is administered, the human subject is identified as having a mutation in the BRAF gene prior to treatment. For example, the human subject can optionally be identified as having the V600E, R461I, I462S, G463E, G463V, G465A, G465E, G465V, G468A, G468E, N580S, E585K, D593V, F594L, G595R, L596V, T598I, V599D, V599E, V599K, V599R, V600K, and/or A727V mutation in the BRAF gene prior to treatment.

In some embodiments wherein a MEK inhibitor is administered, the human subject is identified as having a mutation in the NRAS gene prior to treatment.

In some embodiments wherein an anti-cancer agent is administered, the human subject is identified as having poor responsiveness to treatment with the anti-cancer agent prior to initiating administration of the one or more bacteria and/or the one or more prebiotics.

In some embodiments of the foregoing aspects, the gut microbiome of the human subject is evaluated prior to the initiation of treatment.

In some embodiments of the foregoing aspects, the cancer is melanoma, lung cancer (e.g., small cell lung cancer or non-small cell lung cancer), prostate cancer, bladder cancer, brain cancer, breast cancer, colon cancer, fibrosarcoma, ovarian cancer, a lymphoma, or plasmacytoma.

In some embodiments of the foregoing aspects, the composition is administered orally.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, the exemplary methods and materials are described below. All publications, patent applications, patents, and other references mentioned herein are incorporated by reference in their entirety. In case of conflict, the present application, including definitions, will control. The materials, methods, and examples are illustrative only and not intended to be limiting.

The following are examples of the practice of the invention. They are not to be construed as limiting the scope of the invention in any way.

BRIEF DESCRIPTION OF THE DRAWINGS

FIG. 1A depicts growth of YUMM1.5 (BrafV600E::PTEN−/−::Cdkn2a−/−) melanoma cells after subcutaneous (s.c.) injection of (106) cells into WT or Rnf5−/− mice (n=5). FIG. 1B depicts quantification of tumor-infiltrating effector (CD44hi) CD4+ and CD8+ T cells and total CD45+ cells on day 24 after tumor injection (n=5). FIG. 1C depicts quantification of tumor-infiltrating TNF-α-, IFN-γ and IL-2-producing CD4+ and CD8+ T cells on day 24 after tumor inoculation (n=5). FIG. 1D depicts quantification of tumor-infiltrating total DCs, pDCs, mDCs, and CD8α+ DCs on day 24 after tumor inoculation (n=5). FIG. 1E depicts expression (mean fluorescence intensity, MFI) of MHC class II, CD40, CD80, and CD86 on tumor-infiltrating DCs (CD45+ CD11c+) on day 24 after tumor inoculation (n=5). FIG. 1F depicts growth of YUMM1.5 melanoma cells in lethally irradiated bone marrow-reconstituted WT or Rnf5−/− mice (arrow indicates bone marrow donor→recipient; n=7). FIGS. 1G and 1H depicts growth of YUMM1.5 melanoma cells in mice injected i.p. with control IgG or anti-CD4 or anti-CD8 GoInVivo depleting antibodies (BioLegend) on days 0, 3, 6, 11, 16 (n=9).

FIG. 2A depicts elimination of tumor growth suppression in $Rnf5^{-/-}$ mice by treatment with an antibiotic cocktail administered for 2 weeks prior to tumor cell injection (n=5). FIG. 2B depicts growth of YUMM1.5 melanoma cells in WT or $Rnf5^{-/-}$ mice alone or after co-housing (mixed) for 4 weeks prior to tumor inoculation (alone, n=15; mixed, n=16). FIG. 2C depicts quantification of effector ($CD44^{hi}$) $CD4^+$ and $CD8^+$ T cells, total $CD45^+$ cells, and IFN-γ, TNF-α producing $CD4^+$ and $CD8^+$ T cells in tumors from WT or $Rn5^{-/-}$ mice co-housed for 4 weeks prior to tumor inoculation (n=10). FIG. 2D depicts quantification of tumor-infiltrating total DCs, pDCs, and mDCs in WT or $Rnf5^{-/-}$ mice alone or after co-housing for 4 weeks prior to tumor inoculation (n=10).

FIG. 3A contains representative micrographs of immunohistochemical (IHC) staining of BiP in jejunum, ileum and colon of YUMM1.5 tumor-bearing WT mice or $Rnf5^{-/-}$ mice (scale bar=25 μm). Lower panel present quantification of IHC staining (n=12 fields per group). Staining was scored semi-quantitatively on a four-tier scale from 0 (absent) to 3 (strong membranous and cytoplasmic staining). Intensity scores were multiplied by percentage of intestine cells staining to generate an H score (maximum score, 300). FIG. 3B contains representative micrographs of IHC staining of mucin 2 in jejunum, ileum and colon of YUMM1.5 tumor-bearing WT mice or $Rnf5^{-/-}$ mice (scale bar=25 μm). Mucin 2+ intestinal epithelial cells (IECs) were counted per crypt in the jejunum, ileum and colon following IHC (n=20 fields per group). FIG. 3C depicts villi length and crypt depth calculated from H&E-stained sections of intestines from YUMM1.5 tumor-bearing WT (n=30) or $Rnf5^{-/-}$ (n=32) mice. FIG. 3D depicts serum cytokines in naïve WT or $Rnf5^{-/-}$ mice (n=12). FIG. 3E depicts serum cytokines in WT or $Rnf5^{-/-}$ mice 10 days after tumor inoculation (n=10). FIG. 3F depicts quantification of OT-I $CD8^+$ T cells in the tumor-draining lymph nodes (TdLN) and non-draining lymph nodes (ndLN) of $CD45.1^+$ WT and $Rnf5^{-/-}$ mice injected with B16-OVA melanoma cells. Right dot plots show gating of $CD45.1^+$ $CD8^+$ cells (WT group: n=6, $Rnf5^{-/-}$ group: n=5).

FIGS. 4A-4F are graphs demonstrating that mucin and inulin attenuate melanoma growth. FIG. 4A depicts plots of human fecal samples cultivated under anaerobic conditions in chemically defined medium with or without exogenous carbohydrate (n=6). Relative abundance of taxa encoding extensive glycosyl hydrolase activities. Cultures with no exogenous sugar were compared to cultures with N-acetyl-mannosamine, galactomannan and porcine gastric mucin. FIG. 4B depicts bacterial taxa exhibiting significant differences in relative abundance prior and following tumor growth in WT and $Rnf5^{-/-}$ mice used for in silico simulations. FIG. 4C depicts computer simulation identifies the uptake rates of mucin and inulin degradation products in the 2 media predicted to sustain the WT and $Rnf5^{-/-}$ communities, showing higher predicted consumption of mucin and inulin products in the $Rnf5^{-/-}$ community. FIG. 4D depicts YUMM1.5 tumor growth in WT or $Rnf5^{-/-}$ mice provided with 0 or 3% mucin in drinking water starting 14 days prior to tumor inoculation (n=15). FIG. 4E depicts growth of Yumm1.5 tumors in WT or $Rnf5^{-/-}$ received a control diet or a diet enriched 15% inulin 14 days prior to and during tumor inoculation (n=15). FIG. 4F depicts fold-changes of median abundances between $Rnf5^{-/-}$, mucin and inulin treated and WT mice, for 30 taxa that discriminate tumor attenuating and non-attenuating phenotypes.

FIG. 6A depicts growth of SW1 TLR4-mutant tumor cells in C3H/HeJ TLR4 mutant mice provided with control diet, alone or with supplemented mucin or inulin starting 14 days prior to tumor inoculation (n=10). FIG. 6B depicts growth of MC-38 tumors in C57BL/6 mice (n=10) that received, starting 14 days prior to tumor inoculation, control diet, alone or with supplemented mucin or inulin. FIG. 6C depicts tumor volume in C57BL/6 mice (n=10 per group) injected (s.c.) with a melanoma cell line (N-Ras mutant; $1 \times 10^6$ cells). The mice were provided control or inulin or mucin supplemented diet. When tumors reached a volume of 10-20 $mm^2$, mice were treated with MEKi (PD325901) administered by gavage (10 mg/kg, daily), alone or in combination with inulin or mucin, as indicated. Tumor volume was assessed every 4 days.

DETAILED DESCRIPTION

Figure 1A:
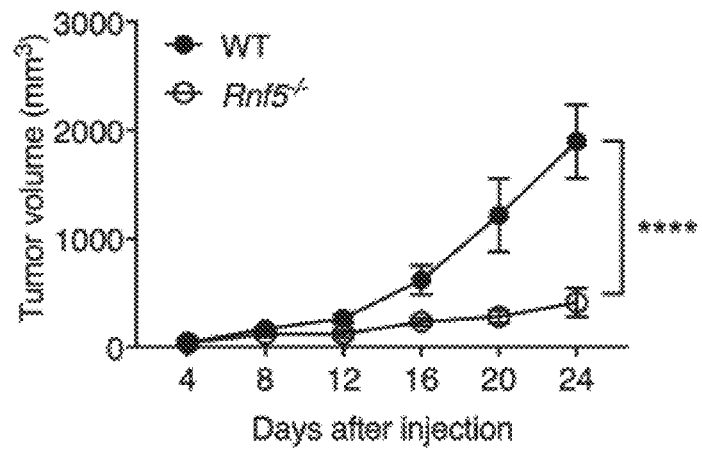
FIGS. 1A-1H are graphs depicting an enhanced anti-tumor immune responses in Rnf5−/− mice.

The accompanying Examples demonstrate an unexpected role for the ubiquitin ligase, RNF5, in regulating the gut microbiota composition and the immune response to tumors. Growth of mouse melanoma cells in vivo is attenuated, while tumor infiltration of $CD4^+$/$CD8^+$ T cells and dendritic cells is increased, in $Rnf5^{-/-}$ mice, resembling changes seen upon immune checkpoint therapy. This phenotype was immune system intrinsic and linked to increased ER stress, intestinal inflammation and mucin production by intestinal epithelial cells. Notably, co-housing of $Rnf5^{-/-}$ and wild-type mice largely abolished these phenotypes, pointing to a microbiota-dependent immune checkpoint activity. Mucin- or inulin-fed wild-type mice phenocopied $Rnf5^{-/-}$ mice, exhibiting increased tumor infiltration of immune cells and reduced tumor growth, pointing to prebiotics that may resemble anti-CTLA-4 therapy.

The bacterial compositions and prebiotic compositions described herein can be used in methods of treating cancer, wherein a therapeutically effective amount of a bacterial composition and/or a prebiotic composition is administered to a human subject that has cancer. Many types of cancer can be treated, including but not limited to melanoma, lung cancer (e.g., small cell lung cancer or non-small cell lung cancer), prostate cancer, bladder cancer, brain cancer, breast cancer, colon cancer, fibrosarcoma, ovarian cancer, a lymphoma, or plasmacytoma.

Bacterial Compositions

A bacterial composition used in the methods described herein contains a therapeutically effective amount of one or more bacteria selected from the group consisting of: (a) *Oscillibacter valericigenes, Acetatifactor muris, Alistipes putredinis, Alistipes finegoldii, Clostridium clostridioforme, Lactobacillus animalis, Lactobacillus murinus, Bacteroides massiliensis, Bacteroides sartorii, Muribaculum intestinale, Parasutterella excrementihominis, Clostridium methylpentosum*, and *Bacteroides rodentium*; or (b) *Bacteroides acidifaciens, Bacteroides xylanisolvens, Bacteroides chinchilla (B. sartorii), B. thetaiotaomicron, B. fragilis, Dysgonomonas wimpennyi, Parabacteroides merdae, Flavobacterium, Staphylococcus* spp., *Staphylococcus sciuri, Staphylococcus xylosus, Helicobacter ganmani, Helicobacter hepaticus, Enterobacter hormaechei, Porphyromonas canis, Porphyromonas gingivicanis, Rickenella microfusus, Olivibacter* spp, *P. goldsteinii, P. koreensis, Pedobacter* spp., *O. sinus, Blautia hansenii*, and *Lachnospira pectinoschiza*.

A bacterial composition can be administered to a subject as, for example, a medical food, a nutraceutical, or a nutritional supplement, or a component of a medical food, a nutraceutical, or a nutritional supplement.

A bacterial composition can be administered to a subject, for example, orally or rectally (e.g., into at least one of the terminal ileum and right colon).

In some embodiments, a bacterial composition contains a single species of bacteria selected from the group consisting of: (a) *Oscillibacter valericigenes, Acetatifactor muris, Alistipes putredinis, Alistipes finegoldii, Clostridium clostridioforme, Lactobacillus animalis, Lactobacillus murinus, Bacteroides massiliensis, Bacteroides sartorii, Muribaculum intestinale, Parasutterella excrementihominis, Clostridium methylpentosum*, and *Bacteroides rodentium*; or (b) *Bacteroides acidifaciens, Bacteroides xylanisolvens, Bacteroides chinchilla (B. sartorii), B. thetaiotaomicron, B. fragilis, Dysgonomonas wimpennyi, Parabacteroides merdae, Flavobacterium, Staphylococcus* spp., *Staphylococcus sciuri, Staphylococcus xylosus, Helicobacter ganmani, Helicobacter hepaticus, Enterobacter hormaechei, Porphyromonas canis, Porphyromonas gingivicanis, Rickenella microfusus, Olivibacter* spp, *P. goldsteinii, P. koreensis, Pedobacter* spp., *O. sinus, Blautia hansenii*, and *Lachnospira pectinoschiza*. In other embodiments, a bacterial composition contains two or more species of bacteria selected from the group consisting of: (a) *Oscillibacter valericigenes, Acetatifactor muris, Alistipes putredinis, Alistipes finegoldii, Clostridium clostridioforme, Lactobacillus animalis, Lactobacillus murinus, Bacteroides massiliensis, Bacteroides sartorii, Muribaculum intestinale, Parasutterella excrementihominis, Clostridium methylpentosum*, and *Bacteroides rodentium*; or (b) *Bacteroides acidifaciens, Bacteroides xylanisolvens, Bacteroides chinchilla (B. sartorii), B. thetaiotaomicron, B. fragilis, Dysgonomonas wimpennyi, Parabacteroides merdae, Flavobacterium, Staphylococcus* spp., *Staphylococcus sciuri, Staphylococcus xylosus, Helicobacter ganmani, Helicobacter hepaticus, Enterobacter hormaechei, Porphyromonas canis, Porphyromonas gingivicanis, Rickenella microfusus, Olivibacter* spp, *P. goldsteinii, P. koreensis, Pedobacter* spp., *O. sinus, Blautia hansenii*, and *Lachnospira pectinoschiza*, e.g., 2, 3, 4, 5, 6, 7, 8, 9, 10, or more species of bacteria selected from the group consisting of: (a) *Oscillibacter valericigenes, Acetatifactor muris, Alistipes putredinis, Alistipes finegoldii, Clostridium clostridioforme, Lactobacillus animalis, Lactobacillus murinus, Bacteroides massiliensis, Bacteroides sartorii, Muribaculum intestinale, Parasutterella excrementihominis, Clostridium methylpentosum*, and *Bacteroides rodentium*; or (b) *Bacteroides acidifaciens, Bacteroides xylanisolvens, Bacteroides chinchilla (B. sartorii), B. thetaiotaomicron, B. fragilis, Dysgonomonas wimpennyi, Parabacteroides merdae, Flavobacterium, Staphylococcus* spp., *Staphylococcus sciuri, Staphylococcus xylosus, Helicobacter ganmani, Helicobacter hepaticus, Enterobacter hormaechei, Porphyromonas canis, Porphyromonas gingivicanis, Rickenella microfusus, Olivibacter* spp, *P. goldsteinii, P. koreensis, Pedobacter* spp., *O. sinus, Blautia hansenii*, and *Lachnospira pectinoschiza*.

In some embodiments, the bacterial composition contains no more than 20 species of bacteria selected from the group consisting of: (a) *Oscillibacter valericigenes, Acetatifactor muris, Alistipes putredinis, Alistipes finegoldii, Clostridium clostridioforme, Lactobacillus animalis, Lactobacillus murinus, Bacteroides massiliensis, Bacteroides sartorii, Muribaculum intestinale, Parasutterella excrementihominis, Clostridium methylpentosum*, and *Bacteroides rodentium*; or (b) *Bacteroides acidifaciens, Bacteroides xylanisolvens, Bacteroides chinchilla (B. sartorii), B. thetaiotaomicron, B. fragilis, Dysgonomonas wimpennyi, Parabacteroides merdae, Flavobacterium, Staphylococcus* spp., *Staphylococcus sciuri, Staphylococcus xylosus, Helicobacter ganmani, Helicobacter hepaticus, Enterobacter hormaechei, Porphyromonas canis, Porphyromonas gingivicanis, Rickenella microfusus, Olivibacter* spp, *P. goldsteinii, P. koreensis, Pedobacter* spp., *O. sinus, Blautia hansenii*, and *Lachnospira pectinoschiza*, e.g., 20, 19, 18, 17, 16, 15, 14, 13, 12, 11, 10, 9, 8, 7, 6, 5, 4, 3, 2, or 1 species of bacteria selected from the group consisting of: (a) *Oscillibacter valericigenes, Acetatifactor muris, Alistipes putredinis, Alistipes finegoldii, Clostridium clostridioforme, Lactobacillus animalis, Lactobacillus murinus, Bacteroides massiliensis, Bacteroides sartorii, Muribaculum intestinale, Parasutterella excrementihominis, Clostridium methylpentosum*, and *Bacteroides rodentium*; or (b) *Bacteroides acidifaciens, Bacteroides xylanisolvens, Bacteroides chinchilla (B. sartorii), B. thetaiotaomicron, B. fragilis, Dysgonomonas wimpennyi, Parabacteroides merdae, Flavobacterium, Staphylococcus* spp., *Staphylococcus sciuri, Staphylococcus xylosus, Helicobacter ganmani, Helicobacter hepaticus, Enterobacter hormaechei, Porphyromonas canis, Porphyromonas gingivicanis, Rickenella microfusus, Olivibacter* spp, *P. goldsteinii, P. koreensis, Pedobacter* spp., *O. sinus, Blautia hansenii*, and *Lachnospira pectinoschiza*.

In one example, a bacterial composition contains *Oscillibacter valericigenes* and at least one of *Acetatifactor muris, Alistipes putredinis, Alistipes finegoldii, Clostridium clostridioforme, Lactobacillus animalis, Lactobacillus murinus, Bacteroides massiliensis, Bacteroides sartorii, Muribaculum intestinale, Parasutterella excrementihominis, Clostridium methylpentosum*, or *Bacteroides rodentium*. In some embodiments, the bacterial composition contains no more than 5 species of bacteria. In some embodiments, the bacterial composition contains no more than 4 species of bacteria. In some embodiments, the bacterial composition contains no more than 3 species of bacteria. In some embodiments, the bacterial composition contains no more than 2 species of bacteria.

In another example, a bacterial composition contains *Acetatifactor muris* and at least one of *Oscillibacter valericigenes, Alistipes putredinis, Alistipes finegoldii, Clostridium clostridioforme, Lactobacillus animalis, Lactobacillus murinus, Bacteroides massiliensis, Bacteroides sartorii, Muribaculum intestinale, Parasutterella excrementihominis, Clostridium methylpentosum*, or *Bacteroides*

*rodentium.* In some embodiments, the bacterial composition contains no more than 5 species of bacteria. In some embodiments, the bacterial composition contains no more than 4 species of bacteria. In some embodiments, the bacterial composition contains no more than 3 species of bacteria. In some embodiments, the bacterial composition contains no more than 2 species of bacteria.

In another example, a bacterial composition contains *Alistipes putredinis* and at least one of *Oscillibacter valericigenes, Acetatifactor muris, Alistipes finegoldii, Clostridium clostridioforme, Lactobacillus animalis, Lactobacillus murinus, Bacteroides massiliensis, Bacteroides sartorii, Muribaculum intestinale, Parasutterella excrementihominis, Clostridium methylpentosum,* or *Bacteroides rodentium.* In some embodiments, the bacterial composition contains no more than 5 species of bacteria. In some embodiments, the bacterial composition contains no more than 4 species of bacteria. In some embodiments, the bacterial composition contains no more than 3 species of bacteria. In some embodiments, the bacterial composition contains no more than 2 species of bacteria.

In another example, a bacterial composition contains *Alistipes finegoldii* and at least one of *Oscillibacter valericigenes, Acetatifactor muris, Alistipes putredinis, Clostridium clostridioforme, Lactobacillus animalis, Lactobacillus murinus, Bacteroides massiliensis, Bacteroides sartorii, Muribaculum intestinale, Parasutterella excrementihominis, Clostridium methylpentosum,* or *Bacteroides rodentium.* In some embodiments, the bacterial composition contains no more than 5 species of bacteria. In some embodiments, the bacterial composition contains no more than 4 species of bacteria. In some embodiments, the bacterial composition contains no more than 3 species of bacteria. In some embodiments, the bacterial composition contains no more than 2 species of bacteria.

In another example, a bacterial composition contains *Clostridium clostridioforme* and at least one of *Oscillibacter valericigenes, Acetatifactor muris, Alistipes putredinis, Alistipes finegoldii, Lactobacillus animalis, Lactobacillus murinus, Bacteroides massiliensis, Bacteroides sartorii, Muribaculum intestinale, Parasutterella excrementihominis, Clostridium methylpentosum,* or *Bacteroides rodentium.* In some embodiments, the bacterial composition contains no more than 5 species of bacteria. In some embodiments, the bacterial composition contains no more than 4 species of bacteria. In some embodiments, the bacterial composition contains no more than 3 species of bacteria. In some embodiments, the bacterial composition contains no more than 2 species of bacteria.

In another example, a bacterial composition contains *Lactobacillus animalis* and at least one of *Oscillibacter valericigenes, Acetatifactor muris, Alistipes putredinis, Alistipes finegoldii, Clostridium clostridioforme, Lactobacillus murinus, Bacteroides massiliensis, Bacteroides sartorii, Muribaculum intestinale, Parasutterella excrementihominis, Clostridium methylpentosum,* or *Bacteroides rodentium.* In some embodiments, the bacterial composition contains no more than 5 species of bacteria. In some embodiments, the bacterial composition contains no more than 4 species of bacteria. In some embodiments, the bacterial composition contains no more than 3 species of bacteria. In some embodiments, the bacterial composition contains no more than 2 species of bacteria.

In another example, a bacterial composition contains *Lactobacillus murinus* and at least one of *Oscillibacter valericigenes, Acetatifactor muris, Alistipes putredinis, Alistipes finegoldii, Clostridium clostridioforme, Lactobacillus animalis, Bacteroides massiliensis, Bacteroides sartorii, Muribaculum intestinale, Parasutterella excrementihominis, Clostridium methylpentosum,* or *Bacteroides rodentium.* In some embodiments, the bacterial composition contains no more than 5 species of bacteria. In some embodiments, the bacterial composition contains no more than 4 species of bacteria. In some embodiments, the bacterial composition contains no more than 3 species of bacteria. In some embodiments, the bacterial composition contains no more than 2 species of bacteria.

In another example, a bacterial composition contains *Bacteroides massiliensis* and at least one of *Oscillibacter valericigenes, Acetatifactor muris, Alistipes putredinis, Alistipes finegoldii, Clostridium clostridioforme, Lactobacillus animalis, Lactobacillus murinus, Bacteroides sartorii, Muribaculum intestinale, Parasutterella excrementihominis, Clostridium methylpentosum,* or *Bacteroides rodentium.* In some embodiments, the bacterial composition contains no more than 5 species of bacteria. In some embodiments, the bacterial composition contains no more than 4 species of bacteria. In some embodiments, the bacterial composition contains no more than 3 species of bacteria. In some embodiments, the bacterial composition contains no more than 2 species of bacteria.

In another example, a bacterial composition contains *Bacteroides sartorii* and at least one of *Oscillibacter valericigenes, Acetatifactor muris, Alistipes putredinis, Alistipes finegoldii, Clostridium clostridioforme, Lactobacillus animalis, Lactobacillus murinus, Bacteroides massiliensis, Muribaculum intestinale, Parasutterella excrementihominis, Clostridium methylpentosum,* or *Bacteroides rodentium.* In some embodiments, the bacterial composition contains no more than 5 species of bacteria. In some embodiments, the bacterial composition contains no more than 4 species of bacteria. In some embodiments, the bacterial composition contains no more than 3 species of bacteria. In some embodiments, the bacterial composition contains no more than 2 species of bacteria.

In another example, a bacterial composition contains *Muribaculum intestinale* and at least one of *Oscillibacter valericigenes, Acetatifactor muris, Alistipes putredinis, Alistipes finegoldii, Clostridium clostridioforme, Lactobacillus animalis, Lactobacillus murinus, Bacteroides massiliensis, Bacteroides sartorii, Parasutterella excrementihominis, Clostridium methylpentosum,* or *Bacteroides rodentium.* In some embodiments, the bacterial composition contains no more than 5 species of bacteria. In some embodiments, the bacterial composition contains no more than 4 species of bacteria. In some embodiments, the bacterial composition contains no more than 3 species of bacteria. In some embodiments, the bacterial composition contains no more than 2 species of bacteria.

In another example, a bacterial composition contains *Parasutterella excrementihominis* and at least one of *Oscillibacter valericigenes, Acetatifactor muris, Alistipes putredinis, Alistipes finegoldii, Clostridium clostridioforme, Lactobacillus animalis, Lactobacillus murinus, Bacteroides massiliensis, Bacteroides sartorii, Muribaculum intestinale, Clostridium methylpentosum,* or *Bacteroides rodentium.* In some embodiments, the bacterial composition contains no more than 5 species of bacteria. In some embodiments, the bacterial composition contains no more than 4 species of bacteria. In some embodiments, the bacterial composition contains no more than 3 species of bacteria. In some embodiments, the bacterial composition contains no more than 2 species of bacteria.

In another example, a bacterial composition contains *Clostridium methylpentosum* and at least one of *Oscillibacter valericigenes, Acetatifactor muris, Alistipes putredinis, Alistipes finegoldii, Clostridium clostridioforme, Lactobacillus animalis, Lactobacillus murinus, Bacteroides massiliensis, Bacteroides sartorii, Muribaculum intestinale, Parasutterella excrementihominis*, or *Bacteroides rodentium*. In some embodiments, the bacterial composition contains no more than 5 species of bacteria. In some embodiments, the bacterial composition contains no more than 4 species of bacteria. In some embodiments, the bacterial composition contains no more than 3 species of bacteria. In some embodiments, the bacterial composition contains no more than 2 species of bacteria.

In another example, a bacterial composition contains *Bacteroides rodentium* and at least one of *Oscillibacter valericigenes, Acetatifactor muris, Alistipes putredinis, Alistipes finegoldii, Clostridium clostridioforme, Lactobacillus animalis, Lactobacillus murinus, Bacteroides massiliensis, Bacteroides sartorii, Muribaculum intestinale, Parasutterella excrementihominis*, or *Clostridium methylpentosum*. In some embodiments, the bacterial composition contains no more than 5 species of bacteria. In some embodiments, the bacterial composition contains no more than 4 species of bacteria. In some embodiments, the bacterial composition contains no more than 3 species of bacteria. In some embodiments, the bacterial composition contains no more than 2 species of bacteria.

In another example, a bacterial composition contains *Bacteroides acidifaciens* and at least one of *Bacteroides xylanisolvens, Bacteroides chinchilla (B. sartorii), B. thetaiotaomicron, B. fragilis, Dysgonomonas wimpennyi, Parabacteroides merdae, Flavobacterium, Staphylococcus* spp., *Staphylococcus sciuri, Staphylococcus xylosus, Helicobacter ganmani, Helicobacter hepaticus, Enterobacter hormaechei, Porphyromonas canis, Porphyromonas gingivicanis, Rickenella microfusus, Olivibacter* spp, *P. goldsteinii, P. koreensis, Pedobacter* spp., *O. sinus, Blautia hansenii*, or *Lachnospira pectinoschiza*. In some embodiments, the bacterial composition contains no more than 5 species of bacteria. In some embodiments, the bacterial composition contains no more than 4 species of bacteria. In some embodiments, the bacterial composition contains no more than 3 species of bacteria. In some embodiments, the bacterial composition contains no more than 2 species of bacteria.

In another example, a bacterial composition contains *Bacteroides xylanisolvens* and at least one of *Bacteroides acidifaciens, Bacteroides chinchilla (B. sartorii), B. thetaiotaomicron, B. fragilis, Dysgonomonas wimpennyi, Parabacteroides merdae, Flavobacterium, Staphylococcus* spp., *Staphylococcus sciuri, Staphylococcus xylosus, Helicobacter ganmani, Helicobacter hepaticus, Enterobacter hormaechei, Porphyromonas canis, Porphyromonas gingivicanis, Rickenella microfusus, Olivibacter* spp, *P. goldsteinii, P. koreensis, Pedobacter* spp., *O. sinus, Blautia hansenii*, or *Lachnospira pectinoschiza*. In some embodiments, the bacterial composition contains no more than 5 species of bacteria. In some embodiments, the bacterial composition contains no more than 4 species of bacteria. In some embodiments, the bacterial composition contains no more than 3 species of bacteria. In some embodiments, the bacterial composition contains no more than 2 species of bacteria.

In another example, a bacterial composition contains *Bacteroides chinchilla (B. sartoril)* and at least one of *Bacteroides acidifaciens, Bacteroides xylanisolvens, B. thetaiotaomicron, B. fragilis, Dysgonomonas wimpennyi, Parabacteroides merdae, Flavobacterium, Staphylococcus* spp., *Staphylococcus sciuri, Staphylococcus xylosus, Helicobacter ganmani, Helicobacter hepaticus, Enterobacter hormaechei, Porphyromonas canis, Porphyromonas gingivicanis, Rickenella microfusus, Olivibacter* spp, *P. goldsteinii, P. koreensis, Pedobacter* spp., *O. sinus, Blautia hansenii*, or *Lachnospira pectinoschiza*. In some embodiments, the bacterial composition contains no more than 5 species of bacteria. In some embodiments, the bacterial composition contains no more than 4 species of bacteria. In some embodiments, the bacterial composition contains no more than 3 species of bacteria. In some embodiments, the bacterial composition contains no more than 2 species of bacteria.

In one example, a bacterial composition contains *B. thetaiotaomicron* and at least one of *Bacteroides acidifaciens, Bacteroides xylanisolvens, Bacteroides chinchilla (B. sartorii), B. fragilis, Dysgonomonas wimpennyi, Parabacteroides merdae, Flavobacterium, Staphylococcus* spp., *Staphylococcus sciuri, Staphylococcus xylosus, Helicobacter ganmani, Helicobacter hepaticus, Enterobacter hormaechei, Porphyromonas canis, Porphyromonas gingivicanis, Rickenella microfusus, Olivibacter* spp, *P. goldsteinii, P. koreensis, Pedobacter* spp., *O. sinus, Blautia hansenii*, or *Lachnospira pectinoschiza*. In some embodiments, the bacterial composition contains no more than 5 species of bacteria. In some embodiments, the bacterial composition contains no more than 4 species of bacteria. In some embodiments, the bacterial composition contains no more than 3 species of bacteria. In some embodiments, the bacterial composition contains no more than 2 species of bacteria.

In one example, a bacterial composition contains *B. fragilis* and at least one of *Bacteroides acidifaciens, Bacteroides xylanisolvens, Bacteroides chinchilla (B. sartorii), B. thetaiotaomicron, Dysgonomonas wimpennyi, Parabacteroides merdae, Flavobacterium, Staphylococcus* spp., *Staphylococcus sciuri, Staphylococcus xylosus, Helicobacter ganmani, Helicobacter hepaticus, Enterobacter hormaechei, Porphyromonas canis, Porphyromonas gingivicanis, Rickenella microfusus, Olivibacter* spp, *P. goldsteinii, P. koreensis, Pedobacter* spp., *O. sinus, Blautia hansenii*, or *Lachnospira pectinoschiza*. In some embodiments, the bacterial composition contains no more than 5 species of bacteria. In some embodiments, the bacterial composition contains no more than 4 species of bacteria. In some embodiments, the bacterial composition contains no more than 3 species of bacteria. In some embodiments, the bacterial composition contains no more than 2 species of bacteria.

In one example, a bacterial composition contains *Dysgonomonas wimpennyi* and at least one of *Bacteroides acidifaciens, Bacteroides xylanisolvens, Bacteroides chinchilla (B. sartorii), B. thetaiotaomicron, B. fragilis, Parabacteroides merdae, Flavobacterium, Staphylococcus* spp., *Staphylococcus sciuri, Staphylococcus xylosus, Helicobacter ganmani, Helicobacter hepaticus, Enterobacter hormaechei, Porphyromonas canis, Porphyromonas gingivicanis, Rickenella microfusus, Olivibacter* spp, *P. goldsteinii, P. koreensis, Pedobacter* spp., *O. sinus, Blautia hansenii*, or *Lachnospira pectinoschiza*. In some embodiments, the bacterial composition contains no more than 5 species of bacteria. In some embodiments, the bacterial composition contains no more than 4 species of bacteria. In some embodiments, the bacterial composition contains no more than 3 species of bacteria. In some embodiments, the bacterial composition contains no more than 2 species of bacteria.

In one example, a bacterial composition contains *Parabacteroides merdae* and at least one of *Bacteroides acidifaciens, Bacteroides xylanisolvens, Bacteroides chinchilla* (*B. sartorii*), *B. thetaiotaomicron, B. fragilis, Dysgonomonas wimpennyi, Flavobacterium, Staphylococcus* spp., *Staphylococcus sciuri, Staphylococcus xylosus, Helicobacter ganmani, Helicobacter hepaticus, Enterobacter hormaechei, Porphyromonas canis, Porphyromonas gingivicanis, Rickenella microfusus, Olivibacter* spp, *P. goldsteinii, P. koreensis, Pedobacter* spp., *O. sinus, Blautia hansenii*, or *Lachnospira pectinoschiza*. In some embodiments, the bacterial composition contains no more than 5 species of bacteria. In some embodiments, the bacterial composition contains no more than 4 species of bacteria. In some embodiments, the bacterial composition contains no more than 3 species of bacteria. In some embodiments, the bacterial composition contains no more than 2 species of bacteria.

In one example, a bacterial composition contains *Flavobacterium* and at least one of *Bacteroides acidifaciens, Bacteroides xylanisolvens, Bacteroides chinchilla* (*B. sartorii*), *B. thetaiotaomicron, B. fragilis, Dysgonomonas wimpennyi, Parabacteroides merdae, Staphylococcus* spp., *Staphylococcus sciuri, Staphylococcus xylosus, Helicobacter ganmani, Helicobacter hepaticus, Enterobacter hormaechei, Porphyromonas canis, Porphyromonas gingivicanis, Rickenella microfusus, Olivibacter* spp, *P. goldsteinii, P. koreensis, Pedobacter* spp., *O. sinus, Blautia hansenii*, or *Lachnospira pectinoschiza*. In some embodiments, the bacterial composition contains no more than 5 species of bacteria. In some embodiments, the bacterial composition contains no more than 4 species of bacteria. In some embodiments, the bacterial composition contains no more than 3 species of bacteria. In some embodiments, the bacterial composition contains no more than 2 species of bacteria.

In one example, a bacterial composition contains *Staphylococcus* spp. and at least one of *Bacteroides acidifaciens, Bacteroides xylanisolvens, Bacteroides chinchilla* (*B. sartorii*), *B. thetaiotaomicron, B. fragilis, Dysgonomonas wimpennyi, Parabacteroides merdae, Flavobacterium, Staphylococcus sciuri, Staphylococcus xylosus, Helicobacter ganmani, Helicobacter hepaticus, Enterobacter hormaechei, Porphyromonas canis, Porphyromonas gingivicanis, Rickenella microfusus, Olivibacter* spp, *P. goldsteinii, P. koreensis, Pedobacter* spp., *O. sinus, Blautia hansenii*, or *Lachnospira pectinoschiza*. In some embodiments, the bacterial composition contains no more than 5 species of bacteria. In some embodiments, the bacterial composition contains no more than 4 species of bacteria. In some embodiments, the bacterial composition contains no more than 3 species of bacteria. In some embodiments, the bacterial composition contains no more than 2 species of bacteria.

In one example, a bacterial composition contains *Staphylococcus sciuri* and at least one of *Bacteroides acidifaciens, Bacteroides xylanisolvens, Bacteroides chinchilla* (*B. sartorii*), *B. thetaiotaomicron, B. fragilis, Dysgonomonas wimpennyi, Parabacteroides merdae, Flavobacterium, Staphylococcus* spp., *Staphylococcus xylosus, Helicobacter ganmani, Helicobacter hepaticus, Enterobacter hormaechei, Porphyromonas canis, Porphyromonas gingivicanis, Rickenella microfusus, Olivibacter* spp, *P. goldsteinii, P. koreensis, Pedobacter* spp., *O. sinus, Blautia hansenii*, or *Lachnospira pectinoschiza*. In some embodiments, the bacterial composition contains no more than 5 species of bacteria. In some embodiments, the bacterial composition contains no more than 4 species of bacteria. In some embodiments, the bacterial composition contains no more than 3 species of bacteria. In some embodiments, the bacterial composition contains no more than 2 species of bacteria.

In one example, a bacterial composition contains *Staphylococcus xylosus* and at least one of *Bacteroides acidifaciens, Bacteroides xylanisolvens, Bacteroides chinchilla* (*B. sartorii*), *B. thetaiotaomicron, B. fragilis, Dysgonomonas wimpennyi, Parabacteroides merdae, Flavobacterium, Staphylococcus* spp., *Staphylococcus sciuri, Helicobacter ganmani, Helicobacter hepaticus, Enterobacter hormaechei, Porphyromonas canis, Porphyromonas gingivicanis, Rickenella microfusus, Olivibacter* spp, *P. goldsteinii, P. koreensis, Pedobacter* spp., *O. sinus, Blautia hansenii*, or *Lachnospira pectinoschiza*. In some embodiments, the bacterial composition contains no more than 5 species of bacteria. In some embodiments, the bacterial composition contains no more than 4 species of bacteria. In some embodiments, the bacterial composition contains no more than 3 species of bacteria. In some embodiments, the bacterial composition contains no more than 2 species of bacteria.

In one example, a bacterial composition contains *Helicobacter ganmani* and at least one of *Bacteroides acidifaciens, Bacteroides xylanisolvens, Bacteroides chinchilla* (*B. sartorii*), *B. thetaiotaomicron, B. fragilis, Dysgonomonas wimpennyi, Parabacteroides merdae, Flavobacterium, Staphylococcus* spp., *Staphylococcus sciuri, Staphylococcus xylosus, Helicobacter hepaticus, Enterobacter hormaechei, Porphyromonas canis, Porphyromonas gingivicanis, Rickenella microfusus, Olivibacter* spp, *P. goldsteinii, P. koreensis, Pedobacter* spp., *O. sinus, Blautia hansenii*, or *Lachnospira pectinoschiza*. In some embodiments, the bacterial composition contains no more than 5 species of bacteria. In some embodiments, the bacterial composition contains no more than 4 species of bacteria. In some embodiments, the bacterial composition contains no more than 3 species of bacteria. In some embodiments, the bacterial composition contains no more than 2 species of bacteria.

In one example, a bacterial composition contains *Helicobacter hepaticus* and at least one of *Bacteroides acidifaciens, Bacteroides xylanisolvens, Bacteroides chinchilla* (*B. sartorii*), *B. thetaiotaomicron, B. fragilis, Dysgonomonas wimpennyi, Parabacteroides merdae, Flavobacterium, Staphylococcus* spp., *Staphylococcus sciuri, Staphylococcus xylosus, Helicobacter ganmani, Enterobacter hormaechei, Porphyromonas canis, Porphyromonas gingivicanis, Rickenella microfusus, Olivibacter* spp, *P. goldsteinii, P. koreensis, Pedobacter* spp., *O. sinus, Blautia hansenii*, or *Lachnospira pectinoschiza*. In some embodiments, the bacterial composition contains no more than 5 species of bacteria. In some embodiments, the bacterial composition contains no more than 4 species of bacteria. In some embodiments, the bacterial composition contains no more than 3 species of bacteria. In some embodiments, the bacterial composition contains no more than 2 species of bacteria.

In one example, a bacterial composition contains *Enterobacter hormaechei* and at least one of *Bacteroides acidifaciens, Bacteroides xylanisolvens, Bacteroides chinchilla* (*B. sartorii*), *B. thetaiotaomicron, B. fragilis, Dysgonomonas wimpennyi, Parabacteroides merdae, Flavobacterium, Staphylococcus* spp., *Staphylococcus sciuri, Staphylococcus xylosus, Helicobacter ganmani, Helicobacter hepaticus, Porphyromonas canis, Porphyromonas gingivicanis, Rickenella microfusus, Olivibacter spp, P. goldsteinii, P. koreensis, Pedobacter spp., O. sinus, Blautia hansenii, or Lachnospira pectinoschiza. In some embodiments, the bacterial composition contains no more than 5 species of bacteria. In some embodiments, the bacterial composition contains no more than 4 species of bacteria. In some embodiments, the bacterial composition contains no more than 3 species of bacteria. In some embodiments, the bacterial composition contains no more than 2 species of bacteria.

In one example, a bacterial composition contains *Porphyromonas canis* and at least one of *Bacteroides acidifaciens, Bacteroides xylanisolvens, Bacteroides chinchilla (B. sartorii), B. thetaiotaomicron, B. fragilis, Dysgonomonas wimpennyi, Parabacteroides merdae, Flavobacterium, Staphylococcus* spp., *Staphylococcus sciuri, Staphylococcus xylosus, Helicobacter ganmani, Helicobacter hepaticus, Enterobacter hormaechei, Porphyromonas gingivicanis, Rickenella microfusus, Olivibacter* spp, *P. goldsteinii, P. koreensis, Pedobacter* spp., *O. sinus, Blautia hansenii,* or *Lachnospira pectinoschiza*. In some embodiments, the bacterial composition contains no more than 5 species of bacteria. In some embodiments, the bacterial composition contains no more than 4 species of bacteria. In some embodiments, the bacterial composition contains no more than 3 species of bacteria. In some embodiments, the bacterial composition contains no more than 2 species of bacteria.

In one example, a bacterial composition contains *Porphyromonas gingivicanis* and at least one of *Bacteroides acidifaciens, Bacteroides xylanisolvens, Bacteroides chinchilla (B. sartorii), B. thetaiotaomicron, B. fragilis, Dysgonomonas wimpennyi, Parabacteroides merdae, Flavobacterium, Staphylococcus* spp., *Staphylococcus sciuri, Staphylococcus xylosus, Helicobacter ganmani, Helicobacter hepaticus, Enterobacter hormaechei, Porphyromonas canis, Rickenella microfusus, Olivibacter* spp, *P. goldsteinii, P. koreensis, Pedobacter* spp., *O. sinus, Blautia hansenii,* or *Lachnospira pectinoschiza*. In some embodiments, the bacterial composition contains no more than 5 species of bacteria. In some embodiments, the bacterial composition contains no more than 4 species of bacteria. In some embodiments, the bacterial composition contains no more than 3 species of bacteria. In some embodiments, the bacterial composition contains no more than 2 species of bacteria.

In one example, a bacterial composition contains *Rickenella microfusus* and at least one of *Bacteroides acidifaciens, Bacteroides xylanisolvens, Bacteroides chinchilla (B. sartorii), B. thetaiotaomicron, B. fragilis, Dysgonomonas wimpennyi, Parabacteroides merdae, Flavobacterium, Staphylococcus* spp., *Staphylococcus sciuri, Staphylococcus xylosus, Helicobacter ganmani, Helicobacter hepaticus, Enterobacter hormaechei, Porphyromonas canis, Porphyromonas gingivicanis, Olivibacter* spp, *P. goldsteinii, P. koreensis, Pedobacter* spp., *O. sinus, Blautia hansenii,* or *Lachnospira pectinoschiza*. In some embodiments, the bacterial composition contains no more than 5 species of bacteria. In some embodiments, the bacterial composition contains no more than 4 species of bacteria. In some embodiments, the bacterial composition contains no more than 3 species of bacteria. In some embodiments, the bacterial composition contains no more than 2 species of bacteria.

In one example, a bacterial composition contains *Olivibacter* spp and at least one of *Bacteroides acidifaciens, Bacteroides xylanisolvens, Bacteroides chinchilla (B. sartorii), B. thetaiotaomicron, B. fragilis, Dysgonomonas wimpennyi, Parabacteroides merdae, Flavobacterium, Staphylococcus* spp., *Staphylococcus sciuri, Staphylococcus xylosus, Helicobacter ganmani, Helicobacter hepaticus, Enterobacter hormaechei, Porphyromonas canis, Porphyromonas gingivicanis, Rickenella microfusus, P. goldsteinii, P. koreensis, Pedobacter* spp., *O. sinus, Blautia hansenii,* or *Lachnospira pectinoschiza*. In some embodiments, the bacterial composition contains no more than 5 species of bacteria. In some embodiments, the bacterial composition contains no more than 4 species of bacteria. In some embodiments, the bacterial composition contains no more than 3 species of bacteria. In some embodiments, the bacterial composition contains no more than 2 species of bacteria.

In one example, a bacterial composition contains *P. goldsteinii* and at least one of *Bacteroides acidifaciens, Bacteroides xylanisolvens, Bacteroides chinchilla (B. sartorii), B. thetaiotaomicron, B. fragilis, Dysgonomonas wimpennyi, Parabacteroides merdae, Flavobacterium, Staphylococcus* spp., *Staphylococcus sciuri, Staphylococcus xylosus, Helicobacter ganmani, Helicobacter hepaticus, Enterobacter hormaechei, Porphyromonas canis, Porphyromonas gingivicanis, Rickenella microfusus, Olivibacter* spp, *P. koreensis, Pedobacter* spp., *O. sinus, Blautia hansenii,* or *Lachnospira pectinoschiza*. In some embodiments, the bacterial composition contains no more than 5 species of bacteria. In some embodiments, the bacterial composition contains no more than 4 species of bacteria. In some embodiments, the bacterial composition contains no more than 3 species of bacteria. In some embodiments, the bacterial composition contains no more than 2 species of bacteria.

In one example, a bacterial composition contains *P. koreensis* and at least one of *Bacteroides acidifaciens, Bacteroides xylanisolvens, Bacteroides chinchilla (B. sartorii), B. thetaiotaomicron, B. fragilis, Dysgonomonas wimpennyi, Parabacteroides merdae, Flavobacterium, Staphylococcus* spp., *Staphylococcus sciuri, Staphylococcus xylosus, Helicobacter ganmani, Helicobacter hepaticus, Enterobacter hormaechei, Porphyromonas canis, Porphyromonas gingivicanis, Rickenella microfusus, Olivibacter* spp, *P. goldsteinii, Pedobacter* spp., *O. sinus, Blautia hansenii,* or *Lachnospira pectinoschiza*. In some embodiments, the bacterial composition contains no more than 5 species of bacteria. In some embodiments, the bacterial composition contains no more than 4 species of bacteria. In some embodiments, the bacterial composition contains no more than 3 species of bacteria. In some embodiments, the bacterial composition contains no more than 2 species of bacteria.

In one example, a bacterial composition contains *Pedobacter* spp. and at least one of *Bacteroides acidifaciens, Bacteroides xylanisolvens, Bacteroides chinchilla (B. sartorii), B. thetaiotaomicron, B. fragilis, Dysgonomonas wimpennyi, Parabacteroides merdae, Flavobacterium, Staphylococcus* spp., *Staphylococcus sciuri, Staphylococcus xylosus, Helicobacter ganmani, Helicobacter hepaticus, Enterobacter hormaechei, Porphyromonas canis, Porphyromonas gingivicanis, Rickenella microfusus, Olivibacter* spp, *P. goldsteinii, P. koreensis, O. sinus, Blautia hansenii,* or *Lachnospira pectinoschiza*. In some embodiments, the bacterial composition contains no more than 5 species of bacteria. In some embodiments, the bacterial composition contains no more than 4 species of bacteria. In some embodiments, the bacterial composition contains no more than 3 species of bacteria. In some embodiments, the bacterial composition contains no more than 2 species of bacteria.

In one example, a bacterial composition contains *O. sinus* and at least one of *Bacteroides acidifaciens, Bacteroides xylanisolvens, Bacteroides chinchilla (B. sartorii), B. thetaiotaomicron, B. fragilis, Dysgonomonas wimpennyi, Parabacteroides merdae, Flavobacterium, Staphylococcus* spp., *Staphylococcus sciuri, Staphylococcus xylosus, Helicobacter ganmani, Helicobacter hepaticus, Enterobacter hormaechei, Porphyromonas canis, Porphyromonas gingivicanis, Rickenella microfusus, Olivibacter* spp, *P. goldsteinii, P. koreensis, Pedobacter* spp., *Blautia hansenii*, or *Lachnospira pectinoschiza*. In some embodiments, the bacterial composition contains no more than 5 species of bacteria. In some embodiments, the bacterial composition contains no more than 4 species of bacteria. In some embodiments, the bacterial composition contains no more than 3 species of bacteria. In some embodiments, the bacterial composition contains no more than 2 species of bacteria.

In one example, a bacterial composition contains *Blautia hansenii* and at least one of *Bacteroides acidifaciens, Bacteroides xylanisolvens, Bacteroides chinchilla (B. sartorii), B. thetaiotaomicron, B. fragilis, Dysgonomonas wimpennyi, Parabacteroides merdae, Flavobacterium, Staphylococcus* spp., *Staphylococcus sciuri, Staphylococcus xylosus, Helicobacter ganmani, Helicobacter hepaticus, Enterobacter hormaechei, Porphyromonas canis, Porphyromonas gingivicanis, Rickenella microfusus, Olivibacter* spp, *P. goldsteinii, P. koreensis, Pedobacter* spp., *O. sinus*, or *Lachnospira pectinoschiza*. In some embodiments, the bacterial composition contains no more than 5 species of bacteria. In some embodiments, the bacterial composition contains no more than 4 species of bacteria. In some embodiments, the bacterial composition contains no more than 3 species of bacteria. In some embodiments, the bacterial composition contains no more than 2 species of bacteria.

In one example, a bacterial composition contains *Lachnospira pectinoschiza* and at least one of *Bacteroides acidifaciens, Bacteroides xylanisolvens, Bacteroides chinchilla (B. sartorii), B. thetaiotaomicron, B. fragilis, Dysgonomonas wimpennyi, Parabacteroides merdae, Flavobacterium, Staphylococcus* spp., *Staphylococcus sciuri, Staphylococcus xylosus, Helicobacter ganmani, Helicobacter hepaticus, Enterobacter hormaechei, Porphyromonas canis, Porphyromonas gingivicanis, Rickenella microfusus, Olivibacter* spp, *P. goldsteinii, P. koreensis, Pedobacter* spp., *O. sinus*, or *Blautia hansenii*. In some embodiments, the bacterial composition contains no more than 5 species of bacteria. In some embodiments, the bacterial composition contains no more than 4 species of bacteria. In some embodiments, the bacterial composition contains no more than 3 species of bacteria. In some embodiments, the bacterial composition contains no more than 2 species of bacteria.

In some embodiments, the bacterial composition contains 100 million to 500 billion colony-forming units (CFU). In certain embodiments, the bacterial composition contains 100 million to 250 billion CFU. In certain embodiments, the bacterial composition contains 100 million to 100 billion CFU.

A bacterial composition can be prepared in a variety of forms, such as capsules, tablets, suppositories, food, or drink. Optionally, the bacterial composition can include a pharmaceutically acceptable excipient, such as microcrystalline cellulose, mannitol, glucose, defatted milk powder, polyvinylpyrrolidone, starch, and combinations thereof.

The bacterial composition can be prepared as a capsule containing a bacterial species or combination of bacterial species described herein. The capsule can be a hollow capsule formed from substances such as, e.g., gelatin, cellulose, or carbohydrate. The bacterial composition can be formulated such that the bacteria is not exposed to conditions prevalent in the gastrointestinal tract before the colon, e.g., high acidity and digestive enzymes present in the stomach and/or intestine. The capsule can be made from aqueous solutions of gelling agents such as animal protein (e.g., gelatin), plant polysaccharides or derivatives such as carrageenans and modified forms of starch and cellulose. Other ingredients may be added to a gelling agent solution such as plasticizers (e.g., glycerin and or sorbitol), coloring agents, preservatives, disintegrants, flavoring, rice or other starch, glycerin, caramel color, titanium dioxide lubricants, and/or a surface treatment.

The bacterial composition can be prepared as a tablet containing a bacterial species or combination of bacterial species described herein. The tablet can include bacteria and one or more tableting agents, such as dibasic calcium phosphate, stearic acid, croscarmellose, silica, cellulose, and/or a cellulose coating.

The bacterial composition can be prepared as a suppository containing a bacterial species or combination of bacterial species described herein. The suppository can include bacteria and one or more carriers, such as polyethylene glycol, acacia, acetylated monoglycerides, carnuba wax, cellulose acetate phthalate, corn starch, dibutyl phthalate, docusate sodium, gelatin, glycerin, iron oxides, kaolin, lactose, magnesium stearate, methyl paraben, pharmaceutical glaze, povidone, propyl paraben, sodium benzoate, sorbitan monoleate, sucrose talc, titanium dioxide, white wax, and/or coloring agents. The bacterial composition can be prepared as a food or drink, or an additive to a food or drink, containing a bacterial species or combination of bacterial species described herein.

In some embodiments, a bacterial composition contains or is administered in conjunction with a prebiotic described herein.

Prebiotic Compositions

A prebiotic composition used in the methods described herein contains a therapeutically effective amount of one or more prebiotics that promote the growth of one or more bacteria selected from the group consisting of: (a) *Oscillibacter valericigenes, Acetatifactor muris, Alistipes putredinis, Alistipes finegoldii, Clostridium clostridioforme, Lactobacillus animalis, Lactobacillus murinus, Bacteroides massiliensis, Bacteroides sartorii, Muribaculum intestinale, Parasutterella excrementihominis, Clostridium methylpentosum*, and *Bacteroides rodentium*; or (b) *Bacteroides acidifaciens, Bacteroides xylanisolvens, Bacteroides chinchilla (B. sartorii), B. thetaiotaomicron, B. fragilis, Dysgonomonas wimpennyi, Parabacteroides merdae, Flavobacterium, Staphylococcus* spp., *Staphylococcus sciuri, Staphylococcus xylosus, Helicobacter ganmani, Helicobacter hepaticus, Enterobacter hormaechei, Porphyromonas canis, Porphyromonas gingivicanis, Rickenella microfusus, Olivibacter* spp, *P. goldsteinii, P. koreensis, Pedobacter* spp., *O. sinus, Blautia hansenii*, and *Lachnospira pectinoschiza*.

In certain embodiments, the prebiotic composition contains one or more prebiotics selected from the group consisting of a mucin (e.g., porcine gastric mucin), inulin, N-acetyl-D-glucosamine, N-acetyl-D-mannosamine, glucose-1-phosphate, D-fructose, a galactomannan, N-acetyl mannosamine, N-acetylgalactosamine, N-acetylneuraminic acid, N-acetyl glucosamine, galactose, fucose, mannose, human milk oligosaccharides, guar gum, dextrin, α-cellulose, β-D glucan, pectin, corn starch, and potato starch.

In certain embodiments, the prebiotic composition contains N-acetyl-D-glucosamine and N-acetyl-D-mannosamine.

In certain embodiments, the prebiotic composition contains glucose-1-phosphate and D-fructose.

A prebiotic composition can be administered to a subject as, for example, a medical food, a nutraceutical, or a nutritional supplement, or a component of a medical food, a nutraceutical, or a nutritional supplement.

A prebiotic composition can be administered to a subject, for example, orally or rectally (e.g., into at least one of the terminal ileum and right colon).

In some embodiments, a prebiotic composition contains a single prebiotic that promotes the growth of one or more bacteria selected from the group consisting of: (a) *Oscillibacter valericigenes, Acetatifactor muris, Alistipes putredinis, Alistipes finegoldii, Clostridium clostridioforme, Lactobacillus animalis, Lactobacillus murinus, Bacteroides massiliensis, Bacteroides sartorii, Muribaculum intestinale, Parasutterella excrementihominis, Clostridium methylpentosum*, and *Bacteroides rodentium*; or (b) *Bacteroides acidifaciens, Bacteroides xylanisolvens, Bacteroides chinchilla (B. sartorii), B. thetaiotaomicron, B. fragilis, Dysgonomonas wimpennyi, Parabacteroides merdae, Flavobacterium, Staphylococcus* spp., *Staphylococcus sciuri, Staphylococcus xylosus, Helicobacter ganmani, Helicobacter hepaticus, Enterobacter hormaechei, Porphyromonas canis, Porphyromonas gingivicanis, Rickenella microfusus, Olivibacter* spp, *P. goldsteinii, P. koreensis, Pedobacter* spp., *O. sinus, Blautia hansenii*, and *Lachnospira pectinoschiza*.

In some embodiments, a prebiotic composition contains two or more prebiotics that promote the growth of one or more bacteria selected from the group consisting of: (a) *Oscillibacter valericigenes, Acetatifactor muris, Alistipes putredinis, Alistipes finegoldii, Clostridium clostridioforme, Lactobacillus animalis, Lactobacillus murinus, Bacteroides massiliensis, Bacteroides sartorii, Muribaculum intestinale, Parasutterella excrementihominis, Clostridium methylpentosum*, and *Bacteroides rodentium*; or (b) *Bacteroides acidifaciens, Bacteroides xylanisolvens, Bacteroides chinchilla (B. sartorii), B. thetaiotaomicron, B. fragilis, Dysgonomonas wimpennyi, Parabacteroides merdae, Flavobacterium, Staphylococcus* spp., *Staphylococcus sciuri, Staphylococcus xylosus, Helicobacter ganmani, Helicobacter hepaticus, Enterobacter hormaechei, Porphyromonas canis, Porphyromonas gingivicanis, Rickenella microfusus, Olivibacter* spp, *P. goldsteinii, P. koreensis, Pedobacter* spp., *O. sinus, Blautia hansenii*, and *Lachnospira pectinoschiza*, e.g., 2, 3, 4, 5, 6, 7, 8, 9, 10, or more prebiotics that promote the growth of one or more bacteria selected from the group consisting of: (a) *Oscillibacter valericigenes, Acetatifactor muris, Alistipes putredinis, Alistipes finegoldii, Clostridium clostridioforme, Lactobacillus animalis, Lactobacillus murinus, Bacteroides massiliensis, Bacteroides sartorii, Muribaculum intestinale, Parasutterella excrementihominis, Clostridium methylpentosum*, and *Bacteroides rodentium*; or (b) *Bacteroides acidifaciens, Bacteroides xylanisolvens, Bacteroides chinchilla (B. sartorii), B. thetaiotaomicron, B. fragilis, Dysgonomonas wimpennyi, Parabacteroides merdae, Flavobacterium, Staphylococcus* spp., *Staphylococcus sciuri, Staphylococcus xylosus, Helicobacter ganmani, Helicobacter hepaticus, Enterobacter hormaechei, Porphyromonas canis, Porphyromonas gingivicanis, Rickenella microfusus, Olivibacter* spp, *P. goldsteinii, P. koreensis, Pedobacter* spp., *O. sinus, Blautia hansenii*, and *Lachnospira pectinoschiza*. In some embodiments, the prebiotic composition contains no more than 20 prebiotics that promote the growth of one or more bacteria selected from the group consisting of: (a) *Oscillibacter valericigenes, Acetatifactor muris, Alistipes putredinis, Alistipes finegoldii, Clostridium clostridioforme, Lactobacillus animalis, Lactobacillus murinus, Bacteroides massiliensis, Bacteroides sartorii, Muribaculum intestinale, Parasutterella excrementihominis, Clostridium methylpentosum*, and *Bacteroides rodentium*; or (b) *Bacteroides acidifaciens, Bacteroides xylanisolvens, Bacteroides chinchilla (B. sartorii), B. thetaiotaomicron, B. fragilis, Dysgonomonas wimpennyi, Parabacteroides merdae, Flavobacterium, Staphylococcus* spp., *Staphylococcus sciuri, Staphylococcus xylosus, Helicobacter ganmani, Helicobacter hepaticus, Enterobacter hormaechei, Porphyromonas canis, Porphyromonas gingivicanis, Rickenella microfusus, Olivibacter* spp, *P. goldsteinii, P. koreensis, Pedobacter* spp., *O. sinus, Blautia hansenii*, and *Lachnospira pectinoschiza*, e.g., 20, 19, 18, 17, 16, 15, 14, 13, 12, 11, 10, 9, 8, 7, 6, 5, 4, 3, 2, or 1 prebiotic that promotes the growth of one or more bacteria selected from the group consisting of: (a) *Oscillibacter valericigenes, Acetatifactor muris, Alistipes putredinis, Alistipes finegoldii, Clostridium clostridioforme, Lactobacillus animalis, Lactobacillus murinus, Bacteroides massiliensis, Bacteroides sartorii, Muribaculum intestinale, Parasutterella excrementihominis, Clostridium methylpentosum*, and *Bacteroides rodentium*; or (b) *Bacteroides acidifaciens, Bacteroides xylanisolvens, Bacteroides chinchilla (B. sartorii), B. thetaiotaomicron, B. fragilis, Dysgonomonas wimpennyi, Parabacteroides merdae, Flavobacterium, Staphylococcus* spp., *Staphylococcus sciuri, Staphylococcus xylosus, Helicobacter ganmani, Helicobacter hepaticus, Enterobacter hormaechei, Porphyromonas canis, Porphyromonas gingivicanis, Rickenella microfusus, Olivibacter* spp, *P. goldsteinii, P. koreensis, Pedobacter* spp., *O. sinus, Blautia hansenii*, and *Lachnospira pectinoschiza*.

In some embodiments, the prebiotic composition comprises 100 mg to 100 g of prebiotic. In certain embodiments, the prebiotic composition comprises 100 mg to 50 g of prebiotic. In certain embodiments, the prebiotic composition comprises 100 mg to 40 g of prebiotic. In certain embodiments, the prebiotic composition comprises 100 mg to 30 g of prebiotic. In certain embodiments, the prebiotic composition comprises 100 mg to 25 g of prebiotic. In certain embodiments, the prebiotic composition comprises 500 mg to 25 g of prebiotic. In certain embodiments, the prebiotic composition comprises 1 g to 25 g of prebiotic. In certain embodiments, the prebiotic composition comprises 10 g to 25 g of prebiotic.

A prebiotic composition can be prepared in a variety of forms, such as capsules, tablets, suppositories, food, or drink. Optionally, the prebiotic composition can include a pharmaceutically acceptable excipient, such as microcrystalline cellulose, mannitol, glucose, defatted milk powder, polyvinylpyrrolidone, starch, and combinations thereof.

The prebiotic composition can be prepared as a capsule containing a prebiotic or combination of prebiotics described herein. The capsule can be a hollow capsule formed from substances such as, e.g., gelatin, cellulose, or carbohydrate. The prebiotic composition can be formulated such that the prebiotic is not exposed to conditions prevalent in the gastrointestinal tract before the colon, e.g., high acidity and digestive enzymes present in the stomach and/or intestine. The capsule can be made from aqueous solutions of gelling agents such as animal protein (e.g., gelatin), plant polysaccharides or derivatives such as carrageenans and modified forms of starch and cellulose. Other ingredients may be added to a gelling agent solution such as plasticizers (e.g., glycerin and or sorbitol), coloring agents, preservatives, disintegrants, flavoring, rice or other starch, glycerin, caramel color, titanium dioxide lubricants, and/or a surface treatment.

The prebiotic composition can be prepared as a tablet containing a prebiotic or combination of prebiotics described herein. The tablet can include a prebiotic and one or more tableting agents, such as dibasic calcium phosphate, stearic acid, croscarmellose, silica, cellulose, and/or a cellulose coating.

The prebiotic composition can be prepared as a suppository containing a prebiotic or combination of prebiotics described herein. The suppository can include a prebiotic and one or more carriers, such as polyethylene glycol, acacia, acetylated monoglycerides, carnuba wax, cellulose acetate phthalate, corn starch, dibutyl phthalate, docusate sodium, gelatin, glycerin, iron oxides, kaolin, lactose, magnesium stearate, methyl paraben, pharmaceutical glaze, povidone, propyl paraben, sodium benzoate, sorbitan monoleate, sucrose talc, titanium dioxide, white wax, and/or coloring agents.

The prebiotic composition can be prepared as a food or drink, or an additive to a food or drink, containing a prebiotic or combination of prebiotics described herein.

In some embodiments, a prebiotic composition contains or is administered in conjunction with a bacterial species described herein.

Combination Treatment

The bacterial species and prebiotics described herein can be administered together as a combination treatment.

In some embodiments, the subject is administered 100 million to 500 billion CFU of bacteria and 100 mg to 100 g of prebiotic. In some embodiments, the subject is administered 100 million to 250 billion CFU of bacteria and 100 mg to 30 g of prebiotic. In some embodiments, the subject is administered 100 million to 100 billion CFU of bacteria and 1 g to 25 g of prebiotic.

The bacterial species and prebiotics described herein (and combinations thereof) can be administered together with one or more anti-cancer agents, such as immune checkpoint regulator, a BRAF inhibitor, or a MEK inhibitor.

In some embodiments, a composition containing a therapeutically effective amount of one or more bacteria selected from the group consisting of: (a) *Oscillibacter valericigenes, Acetatifactor muris, Alistipes putredinis, Alistipes finegoldii, Clostridium clostridioforme, Lactobacillus animalis, Lactobacillus murinus, Bacteroides massiliensis, Bacteroides sartorii, Muribaculum intestinale, Parasutterella excrementihominis, Clostridium methylpentosum*, and *Bacteroides rodentium*; or (b) *Bacteroides acidifaciens, Bacteroides xylanisolvens, Bacteroides chinchilla (B. sartorii), B. thetaiotaomicron, B. fragilis, Dysgonomonas wimpennyi, Parabacteroides merdae, Flavobacterium, Staphylococcus* spp., *Staphylococcus sciuri, Staphylococcus xylosus, Helicobacter ganmani, Helicobacter hepaticus, Enterobacter hormaechei, Porphyromonas canis, Porphyromonas gingivicanis, Rickenella microfusus, Olivibacter* spp, *P. goldsteinii, P. koreensis, Pedobacter* spp., *O. sinus, Blautia hansenii*, and *Lachnospira pectinoschiza* is administered in combination with an immune checkpoint activator. In one example, the immune checkpoint activator is an agonist of costimulation by CD27 (e.g., an agonist antibody that binds to CD27). In one example, the immune checkpoint activator is an agonist of costimulation by CD40 (e.g., an agonist antibody that binds to CD40). In one example, the immune checkpoint activator is an agonist of costimulation by OX40 (e.g., an agonist antibody that binds to OX40). In one example, the immune checkpoint activator is an agonist of costimulation by GITR (e.g., an agonist antibody that binds to GITR). In one example, the immune checkpoint activator is an agonist of costimulation by CD137 (e.g., an agonist antibody that binds to CD137). In one example, the immune checkpoint activator is an agonist of costimulation by CD28 (e.g., an agonist antibody that binds to CD28). In one example, the immune checkpoint activator is an agonist of costimulation by ICOS (e.g., an agonist antibody that binds to ICOS). In some of these embodiments, the human subject is identified as having poor responsiveness to treatment with the immune checkpoint activator prior to initiating administration of the one or more bacteria.

In some embodiments, a composition containing a therapeutically effective amount of one or more prebiotics that promote the growth of one or more bacteria selected from the group consisting of: (a) *Oscillibacter valericigenes, Acetatifactor muris, Alistipes putredinis, Alistipes finegoldii, Clostridium clostridioforme, Lactobacillus animalis, Lactobacillus murinus, Bacteroides massiliensis, Bacteroides sartorii, Muribaculum intestinale, Parasutterella excrementihominis, Clostridium methylpentosum*, and *Bacteroides rodentium*; or (b) *Bacteroides acidifaciens, Bacteroides xylanisolvens, Bacteroides chinchilla (B. sartorii), B. thetaiotaomicron, B. fragilis, Dysgonomonas wimpennyi, Parabacteroides merdae, Flavobacterium, Staphylococcus* spp., *Staphylococcus sciuri, Staphylococcus xylosus, Helicobacter ganmani, Helicobacter hepaticus, Enterobacter hormaechei, Porphyromonas canis, Porphyromonas gingivicanis, Rickenella microfusus, Olivibacter* spp, *P. goldsteinii, P. koreensis, Pedobacter* spp., *O. sinus, Blautia hansenii*, and *Lachnospira pectinoschiza* is administered in combination with an immune checkpoint activator. In one example, the immune checkpoint activator is an agonist of costimulation by CD27 (e.g., an agonist antibody that binds to CD27). In one example, the immune checkpoint activator is an agonist of costimulation by CD40 (e.g., an agonist antibody that binds to CD40). In one example, the immune checkpoint activator is an agonist of costimulation by OX40 (e.g., an agonist antibody that binds to OX40). In one example, the immune checkpoint activator is an agonist of costimulation by GITR (e.g., an agonist antibody that binds to GITR). In one example, the immune checkpoint activator is an agonist of costimulation by CD137 (e.g., an agonist antibody that binds to CD137). In one example, the immune checkpoint activator is an agonist of costimulation by CD28 (e.g., an agonist antibody that binds to CD28). In one example, the immune checkpoint activator is an agonist of costimulation by ICOS (e.g., an agonist antibody that binds to ICOS). In some of these embodiments, the human subject is identified as having poor responsiveness to treatment with the immune checkpoint activator prior to initiating administration of the one or more prebiotics.

In some embodiments, a composition containing a therapeutically effective amount of one or more bacteria selected from the group consisting of (a) *Oscillibacter valericigenes, Acetatifactor muris, Alistipes putredinis, Alistipes finegoldii, Clostridium clostridioforme, Lactobacillus animalis, Lactobacillus murinus, Bacteroides massiliensis, Bacteroides sartorii, Muribaculum intestinale, Parasutterella excrementihominis, Clostridium methylpentosum*, and *Bacteroides rodentium*; or (b) *Bacteroides acidifaciens, Bacteroides xylanisolvens, Bacteroides chinchilla (B. sartorii), B. thetaiotaomicron, B. fragilis, Dysgonomonas wimpennyi, Parabacteroides merdae, Flavobacterium, Staphylococcus* spp., *Staphylococcus sciuri, Staphylococcus xylosus, Helicobacter ganmani, Helicobacter hepaticus, Enterobacter* hormaechei, Porphyromonas canis, Porphyromonas gingivicanis, Rickenella microfusus, Olivibacter spp, P. goldsteinii, P. koreensis, Pedobacter spp., O. sinus, Blautia hansenii, and Lachnospira pectinoschiza is administered in combination with an immune checkpoint inhibitor. In one example, the immune checkpoint inhibitor is an antagonist of PD-1 (e.g., an antagonist antibody that binds to PD-1). In one example, the immune checkpoint inhibitor is an antagonist of PD-L1 (e.g., an antagonist antibody that binds to PD-L1). In one example, the immune checkpoint inhibitor is an antagonist of CTLA-4 (e.g., an antagonist antibody that binds to CTLA-4). In one example, the immune checkpoint inhibitor is an antagonist of A2AR (e.g., an antagonist antibody that binds to A2AR). In one example, the immune checkpoint inhibitor is an antagonist of B7-H3 (e.g., an antagonist antibody that binds to B7-H3). In one example, the immune checkpoint inhibitor is an antagonist of B7-H4 (e.g., an antagonist antibody that binds to B7-H4). In one example, the immune checkpoint inhibitor is an antagonist of BTLA (e.g., an antagonist antibody that binds to BTLA). In one example, the immune checkpoint inhibitor is an antagonist of IDO (e.g., an antagonist antibody that binds to IDO). In one example, the immune checkpoint inhibitor is an antagonist of KIR (e.g., an antagonist antibody that binds to KIR). In one example, the immune checkpoint inhibitor is an antagonist of LAG3 (e.g., an antagonist antibody that binds to LAG3). In one example, the immune checkpoint inhibitor is an antagonist of TIM-3 (e.g., an antagonist antibody that binds to TIM-3). In one example, the immune checkpoint inhibitor is an antagonist of VISTA (e.g., an antagonist antibody that binds to VISTA). In one example, the immune checkpoint inhibitor is an antagonist of CD160 (e.g., an antagonist antibody that binds to CD160). In one example, the immune checkpoint inhibitor is an antagonist of TIGIT (e.g., an antagonist antibody that binds to TIGIT). In one example, the immune checkpoint inhibitor is an antagonist of PSGL-1 (e.g., an antagonist antibody that binds to PSGL-1). In some of these embodiments, the human subject is identified as having poor responsiveness to treatment with the immune checkpoint inhibitor prior to initiating administration of the one or more bacteria.

In some embodiments, a composition containing a therapeutically effective amount of one or more prebiotics that promote the growth of one or more bacteria selected from the group consisting of (a) *Oscillibacter valericigenes, Acetatifactor muris, Alistipes putredinis, Alistipes finegoldii, Clostridium clostridioforme, Lactobacillus animalis, Lactobacillus murinus, Bacteroides massiliensis, Bacteroides sartorii, Muribaculum intestinale, Parasutterella excrementihominis, Clostridium methylpentosum*, and *Bacteroides rodentium*; or (b) *Bacteroides acidifaciens, Bacteroides xylanisolvens, Bacteroides chinchilla* (*B. sartorii*), *B. thetaiotaomicron, B. fragilis, Dysgonomonas wimpennyi, Parabacteroides merdae, Flavobacterium, Staphylococcus* spp., *Staphylococcus sciuri, Staphylococcus xylosus, Helicobacter ganmani, Helicobacter hepaticus, Enterobacter hormaechei, Porphyromonas canis, Porphyromonas gingivicanis, Rickenella microfusus, Olivibacter* spp, *P. goldsteinii, P. koreensis, Pedobacter* spp., *O. sinus, Blautia hansenii*, and *Lachnospira pectinoschiza* is administered in combination with an immune checkpoint inhibitor. In one example, the immune checkpoint inhibitor is an antagonist of PD-1 (e.g., an antagonist antibody that binds to PD-1). In one example, the immune checkpoint inhibitor is an antagonist of PD-L1 (e.g., an antagonist antibody that binds to PD-L1). In one example, the immune checkpoint inhibitor is an antagonist of CTLA-4 (e.g., an antagonist antibody that binds to CTLA-4). In one example, the immune checkpoint inhibitor is an antagonist of A2AR (e.g., an antagonist antibody that binds to A2AR). In one example, the immune checkpoint inhibitor is an antagonist of B7-H3 (e.g., an antagonist antibody that binds to B7-H3). In one example, the immune checkpoint inhibitor is an antagonist of B7-H4 (e.g., an antagonist antibody that binds to B7-H4). In one example, the immune checkpoint inhibitor is an antagonist of BTLA (e.g., an antagonist antibody that binds to BTLA). In one example, the immune checkpoint inhibitor is an antagonist of IDO (e.g., an antagonist antibody that binds to IDO). In one example, the immune checkpoint inhibitor is an antagonist of KIR (e.g., an antagonist antibody that binds to KIR). In one example, the immune checkpoint inhibitor is an antagonist of LAG3 (e.g., an antagonist antibody that binds to LAG3). In one example, the immune checkpoint inhibitor is an antagonist of TIM-3 (e.g., an antagonist antibody that binds to TIM-3). In one example, the immune checkpoint inhibitor is an antagonist of VISTA (e.g., an antagonist antibody that binds to VISTA). In one example, the immune checkpoint inhibitor is an antagonist of CD160 (e.g., an antagonist antibody that binds to CD160). In one example, the immune checkpoint inhibitor is an antagonist of TIGIT (e.g., an antagonist antibody that binds to TIGIT). In one example, the immune checkpoint inhibitor is an antagonist of PSGL-1 (e.g., an antagonist antibody that binds to PSGL-1). In some of these embodiments, the human subject is identified as having poor responsiveness to treatment with the immune checkpoint inhibitor prior to initiating administration of the one or more prebiotics.

In some embodiments, a composition containing a therapeutically effective amount of one or more bacteria selected from the group consisting of (a) *Oscillibacter valericigenes, Acetatifactor muris, Alistipes putredinis, Alistipes finegoldii, Clostridium clostridioforme, Lactobacillus animalis, Lactobacillus murinus, Bacteroides massiliensis, Bacteroides sartorii, Muribaculum intestinale, Parasutterella excrementihominis, Clostridium methylpentosum*, and *Bacteroides rodentium*; or (b) *Bacteroides acidifaciens, Bacteroides xylanisolvens, Bacteroides chinchilla* (*B. sartorii*), *B. thetaiotaomicron, B. fragilis, Dysgonomonas wimpennyi, Parabacteroides merdae, Flavobacterium, Staphylococcus* spp., *Staphylococcus sciuri, Staphylococcus xylosus, Helicobacter ganmani, Helicobacter hepaticus, Enterobacter hormaechei, Porphyromonas canis, Porphyromonas gingivicanis, Rickenella microfusus, Olivibacter* spp, *P. goldsteinii, P. koreensis, Pedobacter* spp., *O. sinus, Blautia hansenii*, and *Lachnospira pectinoschiza* is administered in combination with an immune checkpoint regulator. In one example, the immune checkpoint regulator is CDX-1127. In one example, the immune checkpoint regulator is TGN1412. In one example, the immune checkpoint regulator is NKTR-214. In one example, the immune checkpoint regulator is MEDI0562. In one example, the immune checkpoint regulator is MEDI6469. In one example, the immune checkpoint regulator is MEDI6383. In one example, the immune checkpoint regulator is JTX-2011. In one example, the immune checkpoint regulator is Keytruda (pembrolizumab). In one example, the immune checkpoint regulator is Opdivo (nivolumab). In one example, the immune checkpoint regulator is Yervoy (ipilimumab). In one example, the immune checkpoint regulator is tremelimumab. In one example, the immune checkpoint regulator is Tecentriq (atezolizumab). In one example, the immune checkpoint regulator is MGA271. In one example, the immune checkpoint regulator is indoximod. In one example, the immune checkpoint regulator is Epacadostat. In one example, the immune checkpoint regulator is lirilumab. In one example, the immune checkpoint regulator is BMS-986016. In one example, the immune checkpoint regulator is MPDL3280A. In one example, the immune checkpoint regulator is avelumab. In one example, the immune checkpoint regulator is durvalumab. In one example, the immune checkpoint regulator is MEDI4736. In one example, the immune checkpoint regulator is MEDI4737. In one example, the immune checkpoint regulator is TRX518. In one example, the immune checkpoint regulator is MK-4166. In one example, the immune checkpoint regulator is urelumab (BMS-663513). In one example, the immune checkpoint regulator is PF-05082566 (PF-2566). In some of these embodiments, the human subject is identified as having poor responsiveness to treatment with the immune checkpoint regulator prior to initiating administration of the one or more bacteria.

In some embodiments, a composition containing a therapeutically effective amount of one or more prebiotics that promote the growth of one or more bacteria selected from the group consisting of (a) *Oscillibacter valericigenes, Acetatifactor muris, Alistipes putredinis, Alistipes finegoldii, Clostridium clostridioforme, Lactobacillus animalis, Lactobacillus murinus, Bacteroides massiliensis, Bacteroides sartorii, Muribaculum intestinale, Parasutterella excrementihominis, Clostridium methylpentosum*, and *Bacteroides rodentium*; or (b) *Bacteroides acidifaciens, Bacteroides xylanisolvens, Bacteroides chinchilla (B. sartorii), B. thetaiotaomicron, B. fragilis, Dysgonomonas wimpennyi, Parabacteroides merdae, Flavobacterium, Staphylococcus* spp., *Staphylococcus sciuri, Staphylococcus xylosus, Helicobacter ganmani, Helicobacter hepaticus, Enterobacter hormaechei, Porphyromonas canis, Porphyromonas gingivicanis, Rickenella microfusus, Olivibacter* spp, *P. goldsteinii, P. koreensis, Pedobacter* spp., *O. sinus, Blautia hansenii*, and *Lachnospira pectinoschiza* is administered in combination with an immune checkpoint regulator. In one example, the immune checkpoint regulator is CDX-1127. In one example, the immune checkpoint regulator is TGN1412. In one example, the immune checkpoint regulator is NKTR-214. In one example, the immune checkpoint regulator is MEDI0562. In one example, the immune checkpoint regulator is MEDI6469. In one example, the immune checkpoint regulator is MEDI6383. In one example, the immune checkpoint regulator is JTX-2011. In one example, the immune checkpoint regulator is Keytruda (pembrolizumab). In one example, the immune checkpoint regulator is Opdivo (nivolumab). In one example, the immune checkpoint regulator is Yervoy (ipilimumab). In one example, the immune checkpoint regulator is tremelimumab. In one example, the immune checkpoint regulator is Tecentriq (atezolizumab). In one example, the immune checkpoint regulator is MGA271. In one example, the immune checkpoint regulator is indoximod. In one example, the immune checkpoint regulator is Epacadostat. In one example, the immune checkpoint regulator is lirilumab. In one example, the immune checkpoint regulator is BMS-986016. In one example, the immune checkpoint regulator is MPDL3280A. In one example, the immune checkpoint regulator is avelumab. In one example, the immune checkpoint regulator is durvalumab. In one example, the immune checkpoint regulator is MEDI4736. In one example, the immune checkpoint regulator is MEDI4737. In one example, the immune checkpoint regulator is TRX518. In one example, the immune checkpoint regulator is MK-4166. In one example, the immune checkpoint regulator is urelumab (BMS-663513). In one example, the immune checkpoint regulator is PF-05082566 (PF-2566). In some of these embodiments, the human subject is identified as having poor responsiveness to treatment with the immune checkpoint regulator prior to initiating administration of the one or more prebiotics.

In some embodiments, a composition containing a therapeutically effective amount of one or more bacteria selected from the group consisting of (a) *Oscillibacter valericigenes, Acetatifactor muris, Alistipes putredinis, Alistipes finegoldii, Clostridium clostridioforme, Lactobacillus animalis, Lactobacillus murinus, Bacteroides massiliensis, Bacteroides sartorii, Muribaculum intestinale, Parasutterella excrementihominis, Clostridium methylpentosum*, and *Bacteroides rodentium*; or (b) *Bacteroides acidifaciens, Bacteroides xylanisolvens, Bacteroides chinchilla (B. sartorii), B. thetaiotaomicron, B. fragilis, Dysgonomonas wimpennyi, Parabacteroides merdae, Flavobacterium, Staphylococcus* spp., *Staphylococcus sciuri, Staphylococcus xylosus, Helicobacter ganmani, Helicobacter hepaticus, Enterobacter hormaechei, Porphyromonas canis, Porphyromonas gingivicanis, Rickenella microfusus, Olivibacter* spp, *P. goldsteinii, P. koreensis, Pedobacter* spp., *O. sinus, Blautia hansenii*, and *Lachnospira pectinoschiza* is administered in combination with a BRAF inhibitor. In one example, the BRAF inhibitor is vemurafenib. In one example, the BRAF inhibitor is dabrafenib. In some of these embodiments, the combination is used to treat melanoma in the human subject. In some of these embodiments, the human subject is identified as having a mutation in the BRAF gene prior to the combination treatment. For example, the human subject can be identified as having the V600E, R461I, I462S, G463E, G463V, G465A, G465E, G465V, G468A, G468E, N580S, E585K, D593V, F594L, G595R, L596V, T598I, V599D, V599E, V599K, V599R, V600K, and/or A727V mutation in the BRAF gene prior to the combination treatment. In some of these embodiments, the human subject is identified as having poor responsiveness to treatment with the BRAF inhibitor prior to initiating administration of the one or more bacteria.

In some embodiments, a composition containing a therapeutically effective amount of one or more prebiotics that promote the growth of one or more bacteria selected from the group consisting of (a) *Oscillibacter valericigenes, Acetatifactor muris, Alistipes putredinis, Alistipes finegoldii, Clostridium clostridioforme, Lactobacillus animalis, Lactobacillus murinus, Bacteroides massiliensis, Bacteroides sartorii, Muribaculum intestinale, Parasutterella excrementihominis, Clostridium methylpentosum*, and *Bacteroides rodentium*; or (b) *Bacteroides acidifaciens, Bacteroides xylanisolvens, Bacteroides chinchilla (B. sartorii), B. thetaiotaomicron, B. fragilis, Dysgonomonas wimpennyi, Parabacteroides merdae, Flavobacterium, Staphylococcus* spp., *Staphylococcus sciuri, Staphylococcus xylosus, Helicobacter ganmani, Helicobacter hepaticus, Enterobacter hormaechei, Porphyromonas canis, Porphyromonas gingivicanis, Rickenella microfusus, Olivibacter* spp, *P. goldsteinii, P. koreensis, Pedobacter* spp., *O. sinus, Blautia hansenii*, and *Lachnospira pectinoschiza* is administered in combination with a BRAF inhibitor. In one example, the BRAF inhibitor is vemurafenib. In one example, the BRAF inhibitor is dabrafenib. In some of these embodiments, the combination is used to treat melanoma in the human subject. In some of these embodiments, the human subject is identified as having a mutation in the BRAF gene prior to the combination treatment. For example, the human subject can be identified as having the V600E, R461I, I462S, G463E, G463V, G465A, G465E, G465V, G468A, G468E, N580S, E585K, D593V, F594L, G595R, L596V, T598I, V599D, V599E, V599K, V599R, V600K, and/or A727V mutation in the BRAF gene prior to the combination treatment. In some of these embodiments, the human subject is identified as having poor responsiveness to treatment with the BRAF inhibitor prior to initiating administration of the one or more prebiotics.

In some embodiments, a composition containing a therapeutically effective amount of one or more bacteria selected from the group consisting of (a) *Oscillibacter valericigenes, Acetatifactor muris, Alistipes putredinis, Alistipes finegoldii, Clostridium clostridioforme, Lactobacillus animalis, Lactobacillus murinus, Bacteroides massiliensis, Bacteroides sartorii, Muribaculum intestinale, Parasutterella excrementihominis, Clostridium methylpentosum,* and *Bacteroides rodentium*; or (b) *Bacteroides acidifaciens, Bacteroides xylanisolvens, Bacteroides chinchilla (B. sartorii), B. thetaiotaomicron, B. fragilis, Dysgonomonas wimpennyi, Parabacteroides merdae, Flavobacterium, Staphylococcus* spp., *Staphylococcus sciuri, Staphylococcus xylosus, Helicobacter ganmani, Helicobacter hepaticus, Enterobacter hormaechei, Porphyromonas canis, Porphyromonas gingivicanis, Rickenella microfusus, Olivibacter* spp, *P. goldsteinii, P. koreensis, Pedobacter* spp., *O. sinus, Blautia hansenii,* and *Lachnospira pectinoschiza* is administered in combination with a MEK inhibitor. In one example, the MEK inhibitor is trametinib. In one example, the MEK inhibitor is cobimetinib. In one example, the MEK inhibitor is binimetinib. In one example, the MEK inhibitor is selumetinib. In one example, the MEK inhibitor is PD-325901. In one example, the MEK inhibitor is CI-1040. In one example, the MEK inhibitor is TAK-733. In some of these embodiments, the combination is used to treat melanoma in the human subject. In some of these embodiments, the human subject is identified as having a mutation in the NRAS gene prior to the combination treatment. In some of these embodiments, the human subject is identified as having poor responsiveness to treatment with the MEK inhibitor prior to initiating administration of the one or more bacteria.

In some embodiments, a composition containing a therapeutically effective amount of one or more prebiotics that promote the growth of one or more bacteria selected from the group consisting of (a) *Oscillibacter valericigenes, Acetatifactor muris, Alistipes putredinis, murinus, Bacteroides massiliensis, Bacteroides sartorii, Muribaculum intestinale, Parasutterella excrementihominis, Clostridium methylpentosum,* and *Bacteroides rodentium*; or (b) *Bacteroides acidifaciens, Bacteroides xylanisolvens, Bacteroides chinchilla (B. sartorii), B. thetaiotaomicron, B. fragilis, Dysgonomonas wimpennyi, Parabacteroides merdae, Flavobacterium, Staphylococcus* spp., *Staphylococcus sciuri, Staphylococcus xylosus, Helicobacter ganmani, Helicobacter hepaticus, Enterobacter hormaechei, Porphyromonas canis, Porphyromonas gingivicanis, Rickenella microfusus, Olivibacter* spp, *P. goldsteinii, P. koreensis, Pedobacter* spp., *O. sinus, Blautia hansenii,* and *Lachnospira pectinoschiza* is administered in combination with a MEK inhibitor. In one example, the MEK inhibitor is trametinib. In one example, the MEK inhibitor is cobimetinib. In one example, the MEK inhibitor is binimetinib. In one example, the MEK inhibitor is selumetinib. In one example, the MEK inhibitor is PD-325901. In one example, the MEK inhibitor is CI-1040. In one example, the MEK inhibitor is TAK-733. In some of these embodiments, the combination is used to treat melanoma in the human subject. In some of these embodiments, the human subject is identified as having a mutation in the NRAS gene prior to the combination treatment. In some of these embodiments, the human subject is identified as having poor responsiveness to treatment with the MEK inhibitor prior to initiating administration of the one or more prebiotics.

In some embodiments, a composition containing a therapeutically effective amount of one or more bacteria selected from the group consisting of (a) *Oscillibacter valericigenes, Acetatifactor muris, Alistipes putredinis, Alistipes finegoldii, Clostridium clostridioforme, Lactobacillus animalis, Lactobacillus murinus, Bacteroides massiliensis, Bacteroides sartorii, Muribaculum intestinale, Parasutterella excrementihominis, Clostridium methylpentosum,* and *Bacteroides rodentium*; or (b) *Bacteroides acidifaciens, Bacteroides xylanisolvens, Bacteroides chinchilla (B. sartorii), B. thetaiotaomicron, B. fragilis, Dysgonomonas wimpennyi, Parabacteroides merdae, Flavobacterium, Staphylococcus* spp., *Staphylococcus sciuri, Staphylococcus xylosus, Helicobacter ganmani, Helicobacter hepaticus, Enterobacter hormaechei, Porphyromonas canis, Porphyromonas gingivicanis, Rickenella microfusus, Olivibacter* spp, *P. goldsteinii, P. koreensis, Pedobacter* spp., *O. sinus, Blautia hansenii,* and *Lachnospira pectinoschiza* is administered in combination with BRAF inhibitor and a MEK inhibitor. In one example, the BRAF inhibitor is vemurafenib or dabrafenib and the MEK inhibitor is trametinib, cobimetinib, binimetinib, selumetinib, PD-325901, CI-1040, or TAK-733. In some of these embodiments, the combination is used to treat melanoma in the human subject. In some of these embodiments, the human subject is identified as having poor responsiveness to treatment with the BRAF inhibitor and the MEK inhibitor prior to initiating administration of the one or more bacteria.

In some embodiments, a composition containing a therapeutically effective amount of one or more prebiotics that promote the growth of one or more bacteria selected from the group consisting of (a) *Oscillibacter valericigenes, Acetatifactor muris, Alistipes putredinis, Alistipes finegoldii, Clostridium clostridioforme, Lactobacillus animalis, Lactobacillus murinus, Bacteroides massiliensis, Bacteroides sartorii, Muribaculum intestinale, Parasutterella excrementihominis, Clostridium methylpentosum,* and *Bacteroides rodentium*; or (b) *Bacteroides acidifaciens, Bacteroides xylanisolvens, Bacteroides chinchilla (B. sartorii), B. thetaiotaomicron, B. fragilis, Dysgonomonas wimpennyi, Parabacteroides merdae, Flavobacterium, Staphylococcus* spp., *Staphylococcus sciuri, Staphylococcus xylosus, Helicobacter ganmani, Helicobacter hepaticus, Enterobacter hormaechei, Porphyromonas canis, Porphyromonas gingivicanis, Rickenella microfusus, Olivibacter* spp, *P. goldsteinii, P. koreensis, Pedobacter* spp., *O. sinus, Blautia hansenii,* and *Lachnospira pectinoschiza* is administered in combination with BRAF inhibitor and a MEK inhibitor. In one example, the BRAF inhibitor is vemurafenib or dabrafenib and the MEK inhibitor is trametinib, cobimetinib, binimetinib, selumetinib, PD-325901, CI-1040, or TAK-733. In some of these embodiments, the combination is used to treat melanoma in the human subject. In some of these embodiments, the human subject is identified as having poor responsiveness to treatment with the BRAF inhibitor and the MEK inhibitor prior to initiating administration of the one or more prebiotics.

The following are examples of the practice of the invention. They are not to be construed as limiting the scope of the invention in any way.

EXAMPLES

Example 1: Anti-Tumor Immune Response in RING Finger Protein 5−/− Mice

Figure 1B:
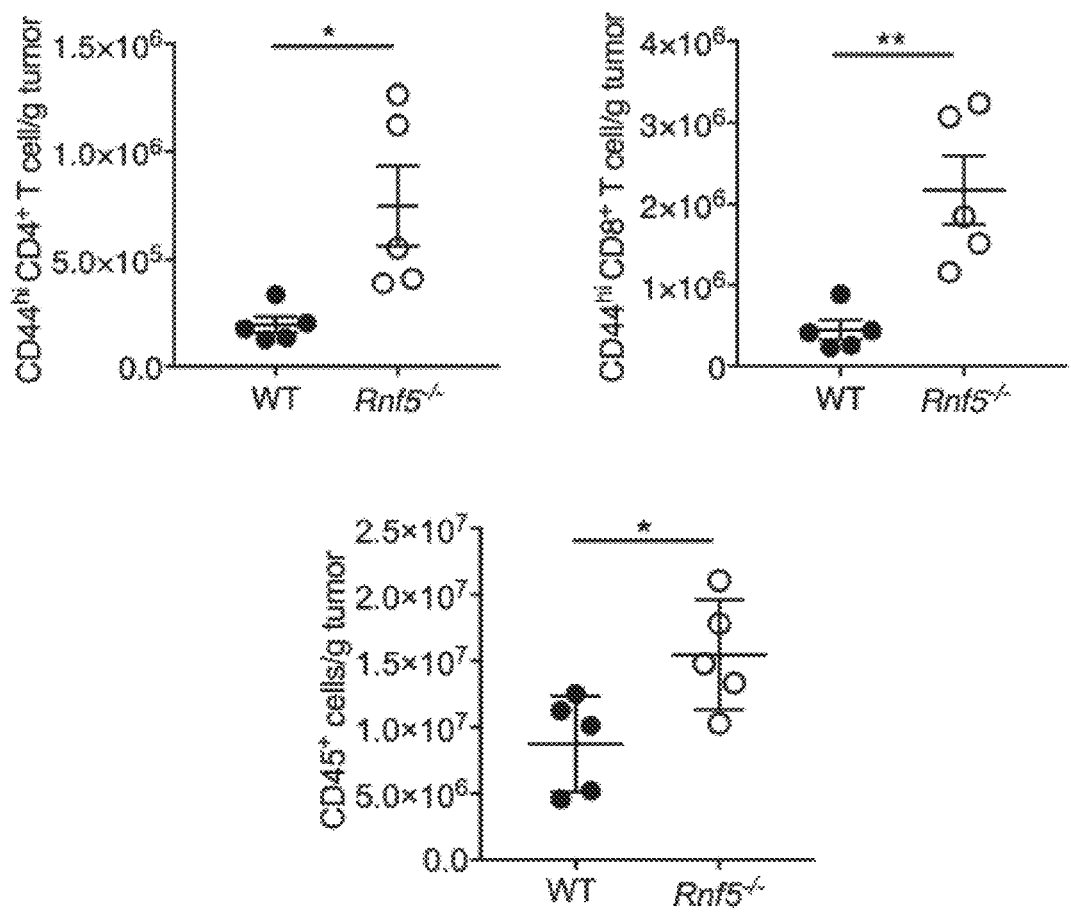
Figure 1C:
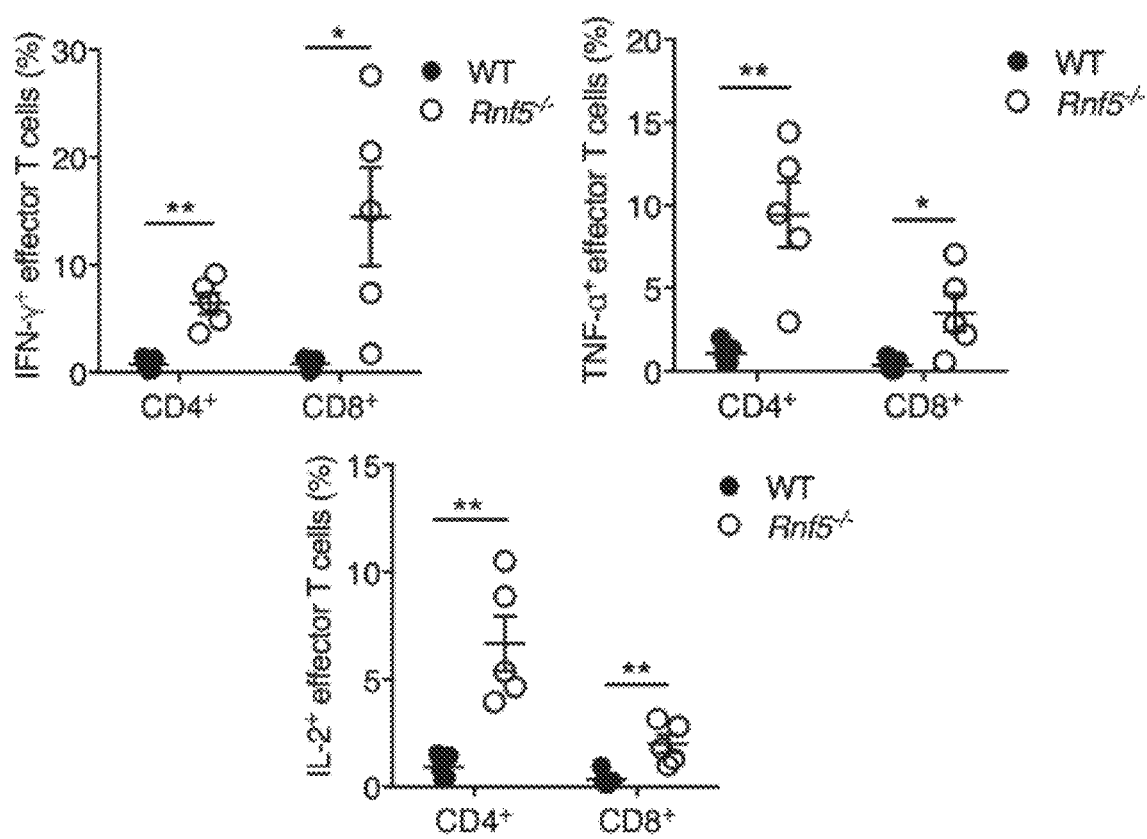
Figure 1D:
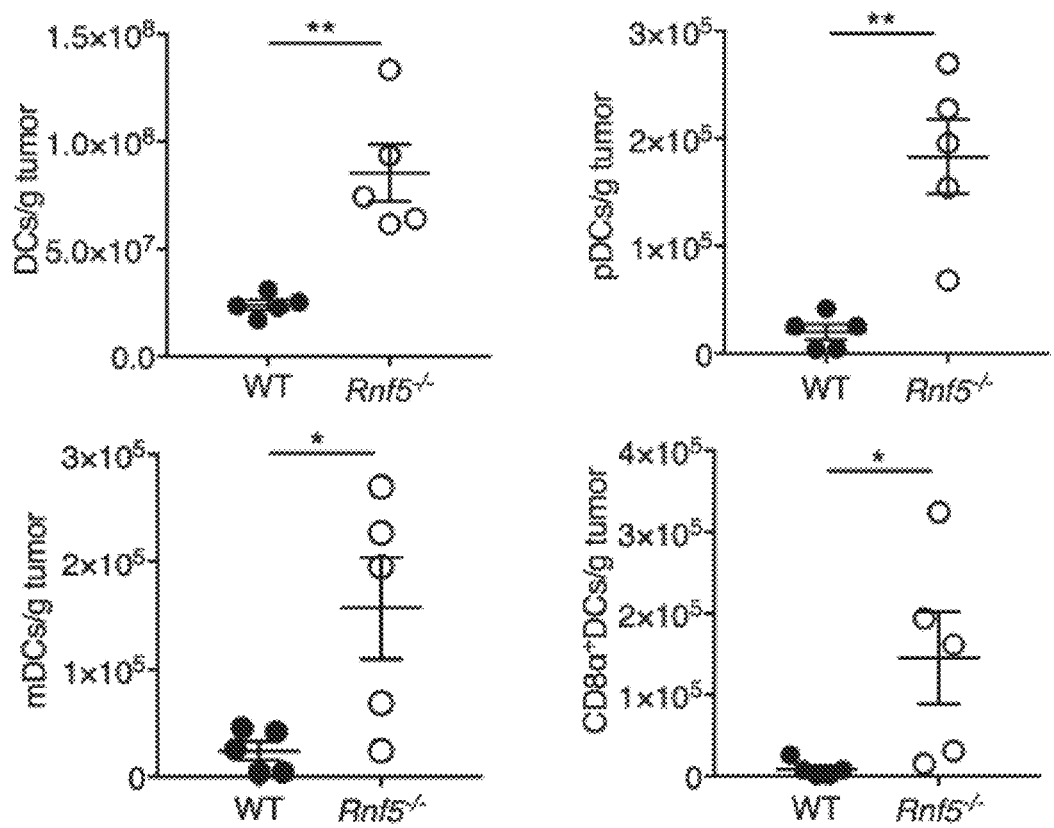
Figure 1E:
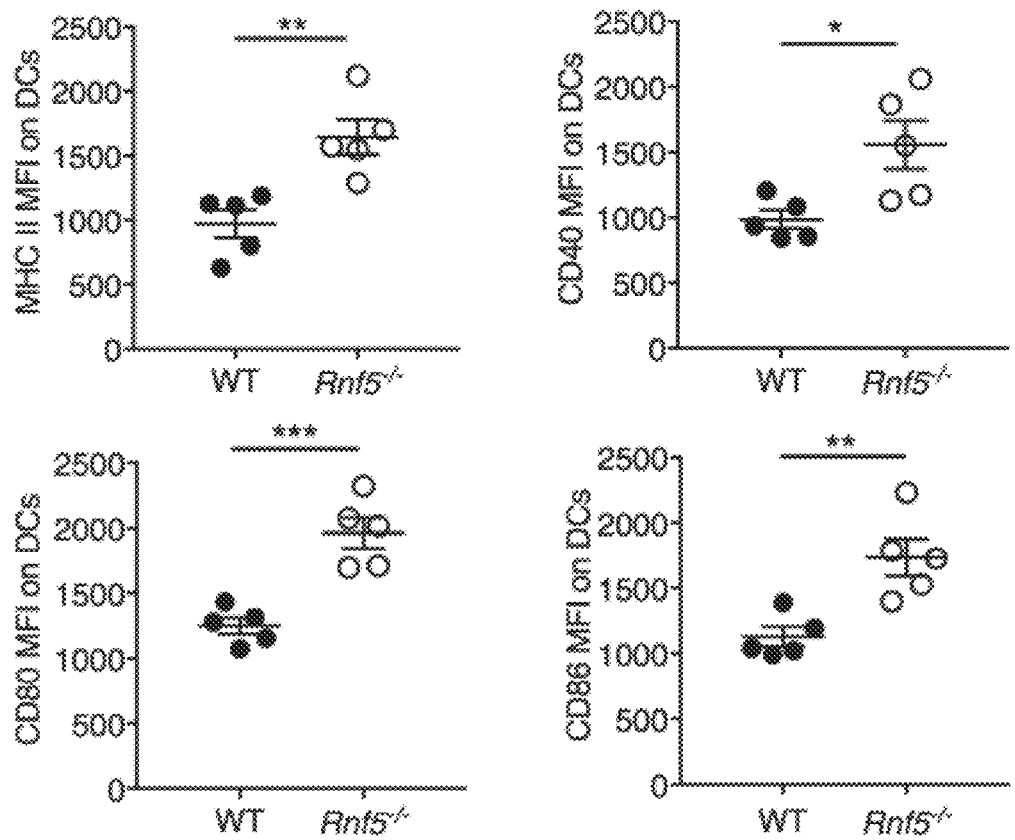

To determine whether RING finger protein $5^{-/-}$ ($Rnf^{-/-}$) mice exhibit altered immune checkpoint function, the growth of mouse melanoma cell lines was evaluated in syngeneic Rnf5$^{-/-}$ C57BL/6 mice. Tumors arising from B16F10, or from YUMM1.3, YUMM1.5 or YUMM1.9, Braf$^{V600E}$::Pten$^{-/-}$::Cdkn2a$^{-/-}$ cell lines, or YUMM1.3 expressing shRNF5, grew more slowly and were significantly smaller in Rnf5$^{-/-}$ mice than in wild-type (WT) mice obtained from crosses of Rnf5 heterozygotes (FIG. 1A). Analysis of tumor-infiltrating cells isolated at 16 and 24 days after cell injection showed markedly higher CD44 effector (CD44$^{hi}$) CD8$^{+}$ and CD4$^{+}$ T cells and CD45$^{+}$ cells in the in tumors from Rnf5$^{-/-}$ mice compared to WT mice (FIG. 1B). Tumor-infiltrating CD4$^{+}$ and CD8$^{+}$ lymphocytes (TILs) from Rnf5$^{-/-}$ mice displayed greater effector function, as indicated by IFN-γ, TNF-α and IL-2 expression (FIG. 1C), suggesting that increased recruitment and TIL effector function underlies the more potent anti-tumor response of Rnf5$^{-/-}$ mice. The inhibitory checkpoint receptors PD-1, TIM-3, and LAG-3 were upregulated on Rnf5$^{-/-}$ CD8$^{+}$ T cells, and PD-L1 expression was upregulated on Rnf5$^{-/-}$ macrophages and dendritic cells (DCs), implying that the stimulated immune status of these mice overcomes checkpoint-mediated inhibition of the anti-tumor response. In support of this, expression of MHC class II and immunostimulatory CD80 and CD86 molecules were higher on tumor infiltrating macrophages from Rnf5$^{-/-}$ mice compared to WT mice; the total number of DCs was higher in tumors from Rnf5$^{-/-}$ mice including myeloid (mDCs) as well as plasmacytoid (pDCs) and CD8alpha$^{+}$ conventional DCs (FIG. 1D). Rnf5$^{-/-}$ DCs also expressed higher levels of MHC class II as well as the costimulatory molecules CD40, CD80, and CD86 (FIG. 1E). These data indicate a clear shift to a proinflammatory tumor microenvironment in Rnf5$^{-/-}$ mice.

Figure 1F:
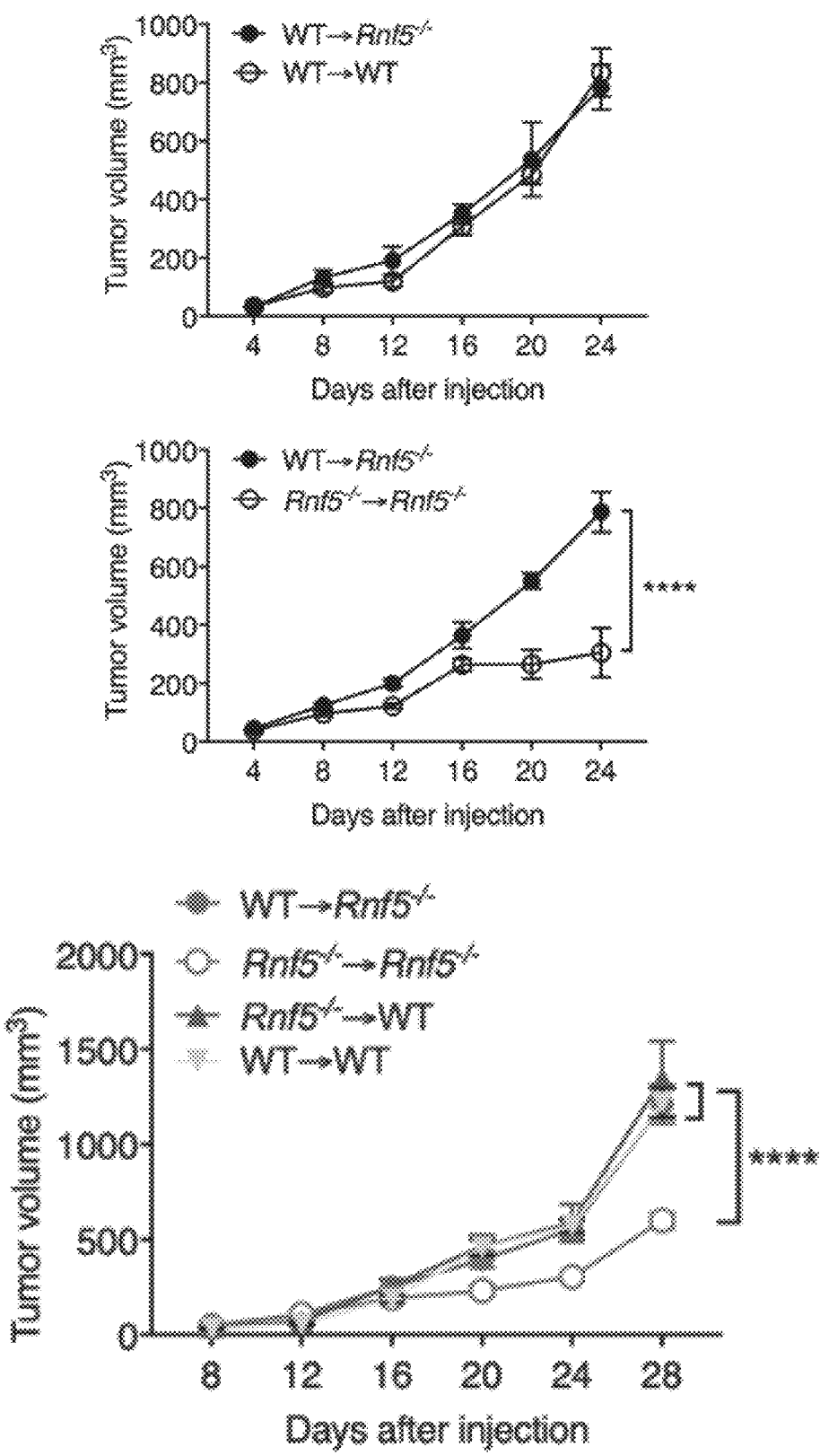
Figure 1G:
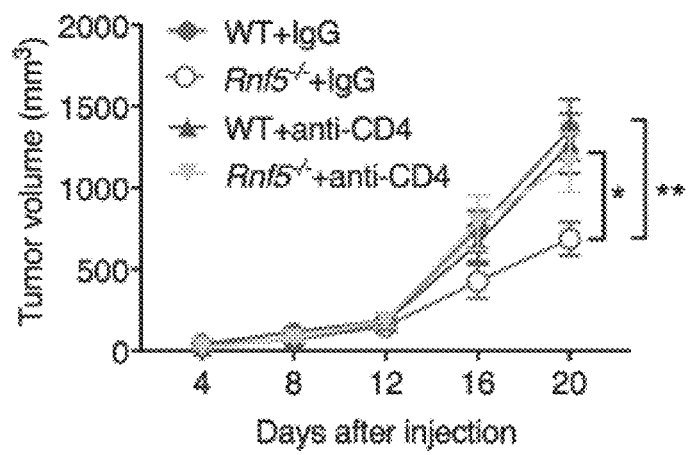
Figure 1H:
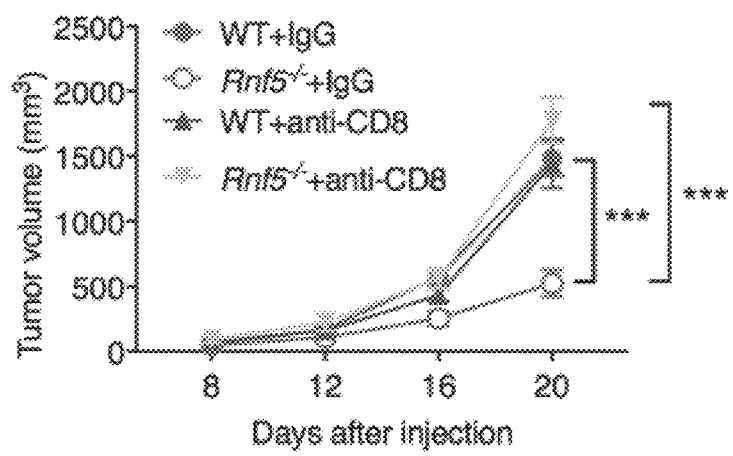

To determine whether the observed "immune checkpoint" phenotype of Rnf5$^{-/-}$ mice was due to RNF5 deficiency in cells from the hematopoietic or stromal compartment, tumor growth was examined in bone marrow chimeras created by injecting WT or Rnf5$^{-/-}$ bone marrow cells into lethally irradiated WT or Rnf5$^{-/-}$ animals. Tumor growth in WT→Rnf5$^{-/-}$ and Rnf5$^{-/-}$→WT chimeras was comparable to that in WT→WT mice, indicating that the absence of RNF5 in both hematopoietic and non-hematopoietic cells is required for the anti-tumor response of Rnf5$^{-/-}$ mice (FIG. 1F). Moreover, depletion of either CD4$^{+}$ (FIG. 1G) or CD8$^{+}$ (FIG. 1H) T cells, but not blockade of PD-1, abrogated the ability of Rnf5$^{-/-}$ mice to inhibit melanoma tumor growth. Collectively, these results point to a critical role for RNF5 in the CD4$^{+}$ and CD8$^{+}$ T cell-dependent anti-tumor immune response.

Example 2: Gut Microbiome is Altered by RNF5 Deficiency

The fecal microbiota of Rnf5$^{-/-}$ and WT mice were analyzed. In an initial analysis, the microbial profiles highlighted several differences prior, and more significantly, following tumor cell injection involving distinct taxonomic groups. Of those, increased relative abundance of several bacterial taxa (including *Bacteroides* spp., *B. acidifaciens*, *B. chinchilla*, *B. xylanisolvens*, *Parabacteroides merdae*, *Porphyromonas canis*, *Rickenella microfusus*) and decreased abundance of others (including unclassified *Bifidobacterium* spp., *B. choerinum*, *Odoribacter denticanis*, *Parabacteroides goldsteinii*, unclassified *Olivibacter*, *Parapedobacter koreensis*) typified the microbiome ofRnf5$^{-/-}$ mice bearing tumors, compared with the WT genotype.

Figure 7:
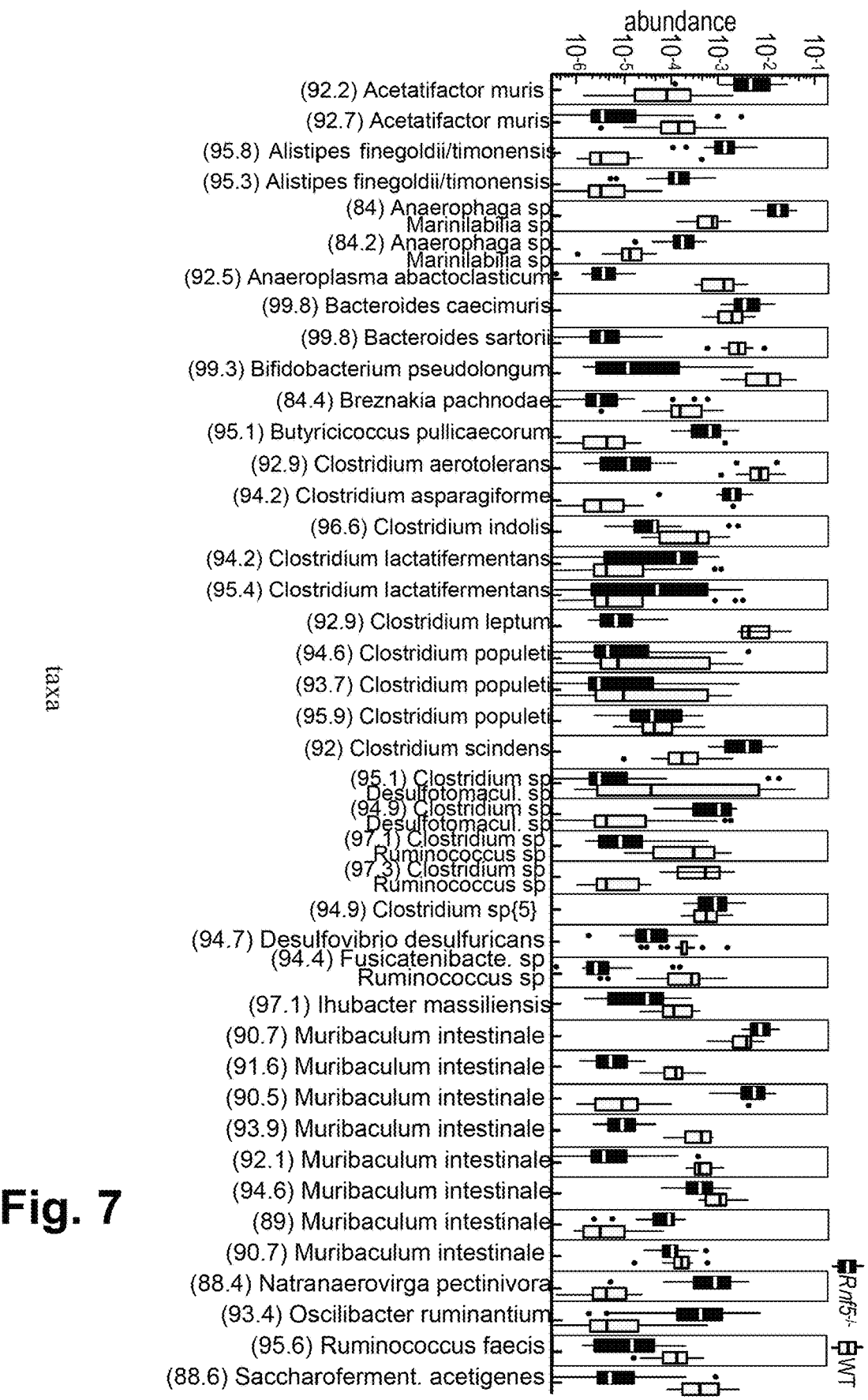
FIG. 7 is a boxplot showing the changes in abundance of the 42 taxa distinguishing WT and $Rnf5^{-/-}$ tumor bearing mice.

The fecal microbiota of Rnf5$-/-$ and WT mice were further analyzed. Marked differences in the microbial profiles were observed, highlighting differences in community structure depicted in principle component analysis that distinctly segregated Rnf5$^{-/-}$ from WT microbiota. Analysis of microbiota allowed the identification of 42 phylotypes that distinguished Rnf5$^{-/-}$ and WT microbiota in tumor bearing mice (FIG. 7). These phylotypes are dominated by a few taxonomic groups, the largest of which fall into the *Clostridium* cluster (37%). All but four of these may be assigned to Clostrium cluster IV or XIVa, known to be capable of producing butyrate that may influence Foxp3$^{+}$ Treg cells expansion. A relatively large portion of the distinguishing taxa are related to *Muribaculm intestinale* (22%) that are phylogenetically similar to the better described *Barnesiella*.

From these studies, the following bacterial strains were identified as being associated with inhibition of tumor growth: *Oscillibacter valericigenes, Acetatifactor muris, Alistipes putredinis, Alistipes finegoldii, Clostridium clostridioforme, Lactobacillus animalis, Lactobacillus murinus, Bacteroides massiliensis, Bacteroides sartorii, Muribaculum intestinale, Parasutterella excrementihominis, Clostridium methylpentosum,* and *Bacteroides rodentium.*

Figure 2A:
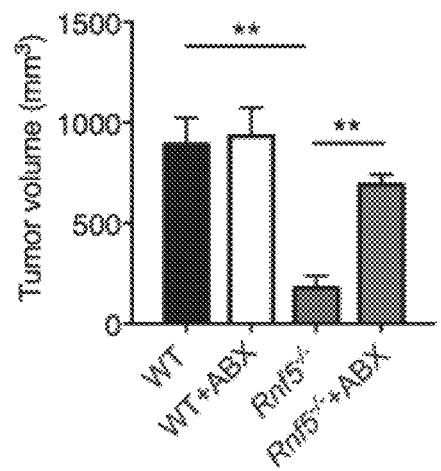
FIGS. 2A-2D are graphs demonstrating that the gut microbiome controls melanoma growth.

These observations prompted us to ask whether the gut microbiome might play a direct role in the immune checkpoint phenotype of Rnf5$^{-/-}$ mice. Treatment of mice with an antibiotic cocktail for two weeks, which is expected to eliminate most gut bacteria, increased the tumor growth rate in Rnf5$^{-/-}$ mice compared with untreated controls, suggesting that the gut microbiome influences tumor growth (FIG. 2A). Co-housing of Rnf5$^{-/-}$ and WT mice prior to tumor cell injection led to a convergence of the gut microbiota, such that Rnf5$^{-/-}$ was more similar to that of WT mice than Rnf5$^{-/-}$ mice housed alone.

Figure 2B:
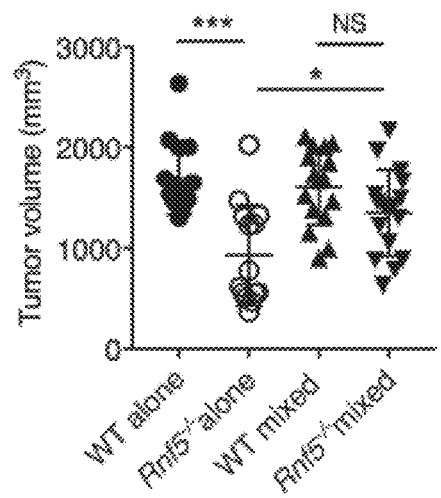
Figure 2C:
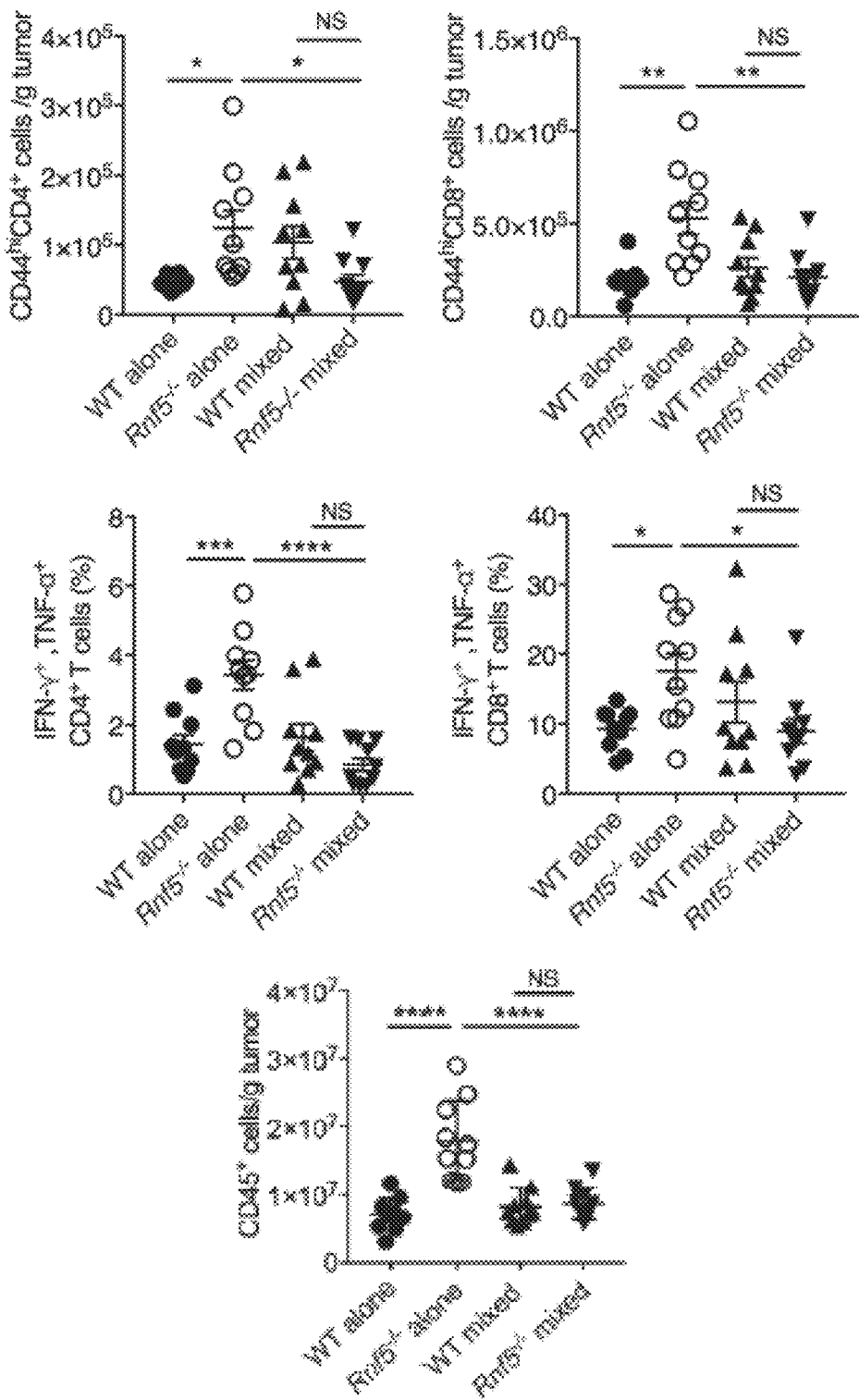
Figure 2D:
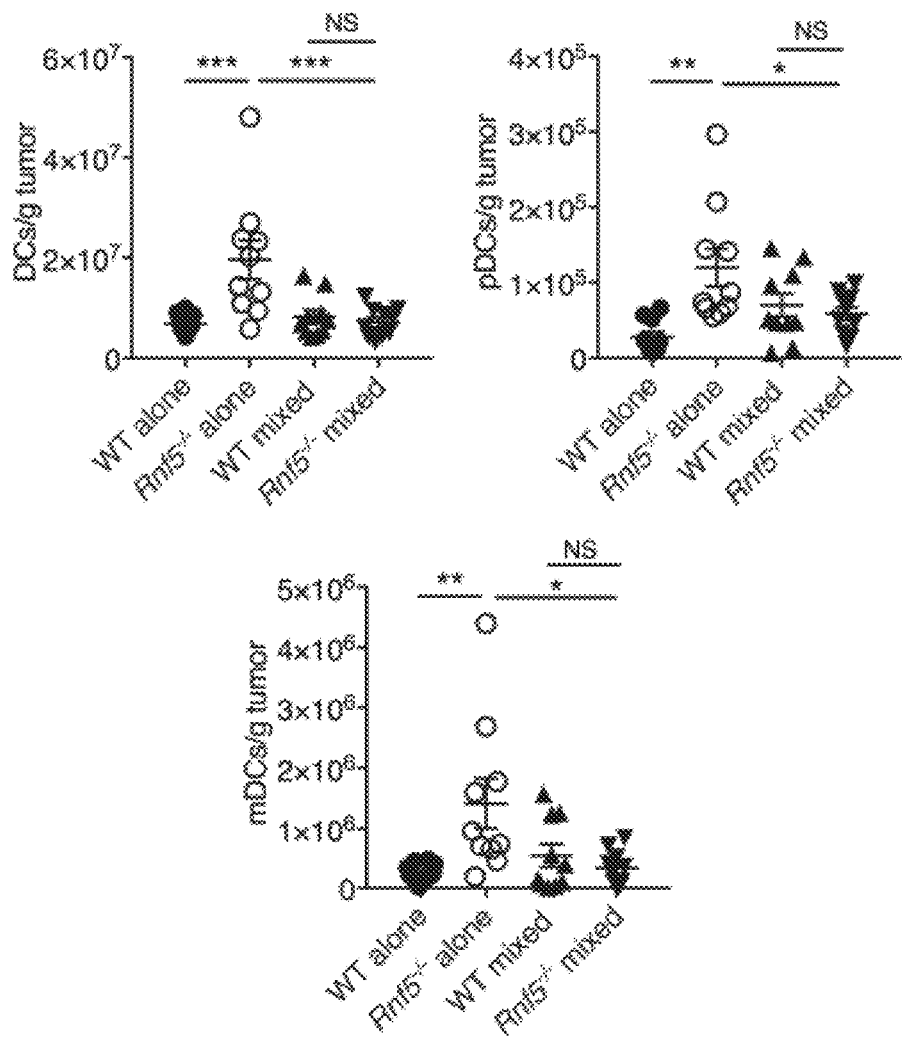

Significantly, co-housing largely eliminated the Rnf5$^{-/-}$ suppression of tumor growth by Rnf5$^{-/-}$ mice (FIG. 2B), concomitant with a reduction in CD44$^{hi}$CD4$^{+}$, CD44$^{hi}$CD8$^{+}$ T cells and CD45$^{+}$ cells, and cytokine production (FIG. 2C) and numbers of DCs and DC subsets (FIG. 2D) and MHC class II expression on DCs. Finally, the differences in PD-1 and LAG-3 expression between TILs from Rnf5$^{-/-}$ and WT mice were eliminated following co-housing. Collectively, these data support a role for cross-talk between the gut microbiota and immune system in the suppression of tumor growth in Rnf5$^{-/-}$ mice.

Example 3: Intrinsic Inflammation Associated with Tumor Inhibition and Microbiome Alteration in Rnf5$^{-/-}$ mice Differences in immunoregulatory gene expression between TILs from WT and Rnf5$^{-/-}$ mice were mapped by performing NanoString analysis of 770 genes expressed by 24 different immune cell types. This analysis identified marked changes in key immune regulatory networks associated with T, NK, DC and macrophage cell function. Interestingly, changes in the expression of chemokines and genes related to antigen presentation and DC function networks pointed to the possible role of Toll like receptors (TLRs) in the phenotype of Rnf5$^{-/-}$ mice. Changes in gene expression identified in the NanoString analysis were confirmed by qPCR analysis of cDNA derived from tumors grown in WT and Rnf5$^{-/-}$ mice.

Figure 3A:
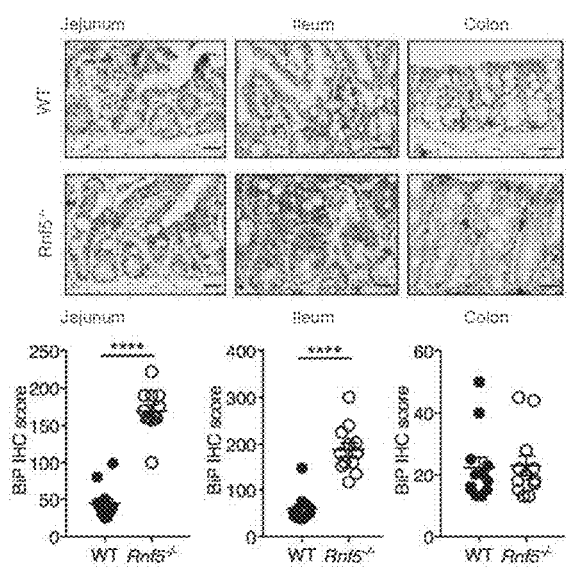
FIGS. 3A-3F are graphs depicting enhanced ER stress, mucin2 expression and reduced vilii length in the intestine of tumor bearing $Rnf5^{-/-}$ mice mice.
Figure 3B:
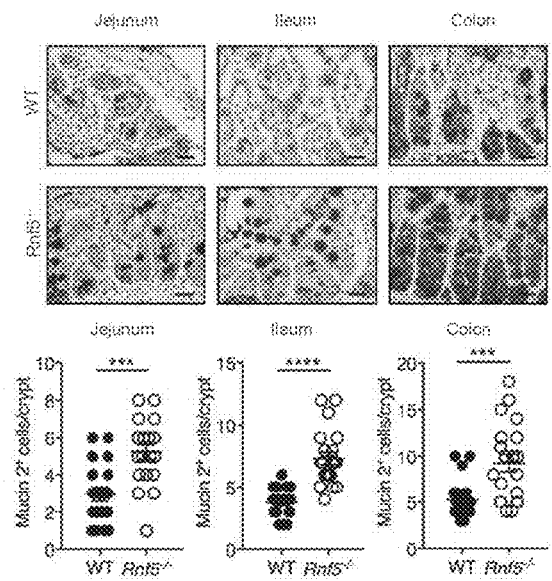
Figure 3C:
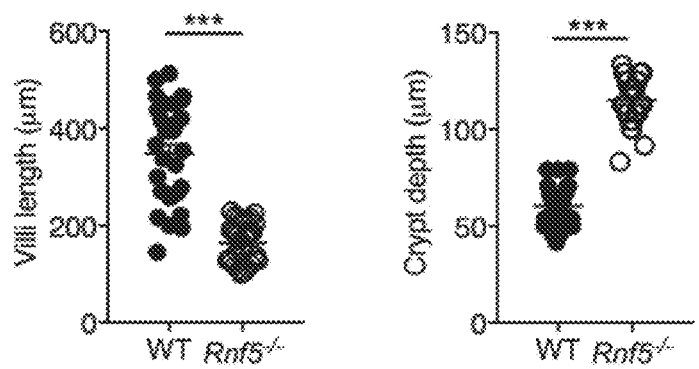
Figure 3D:
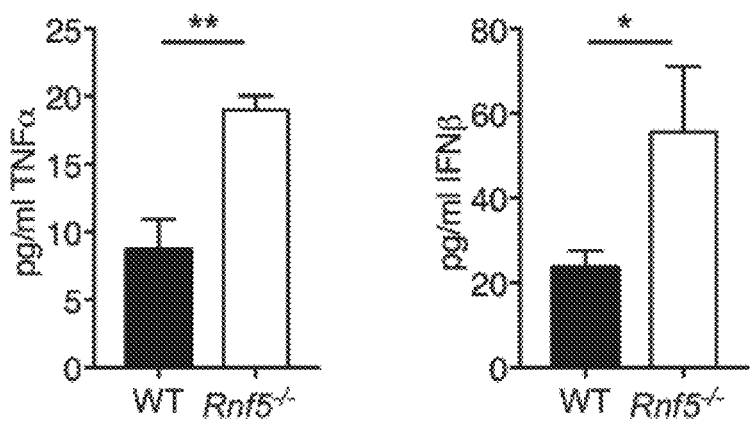
Figure 3E:
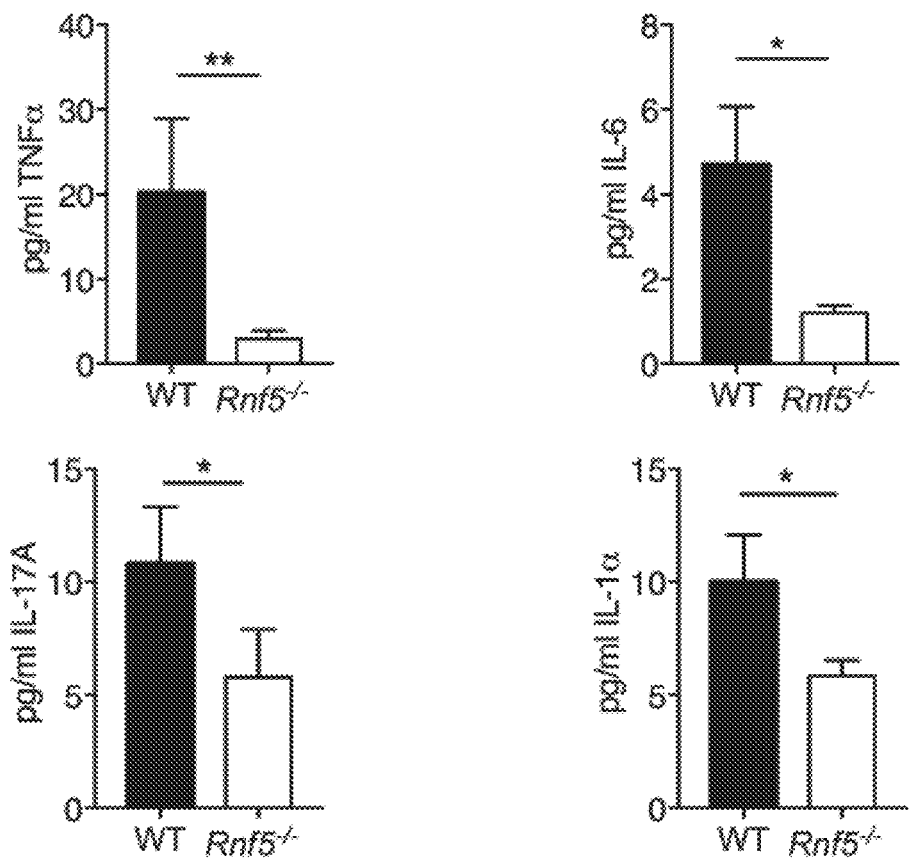

Consistent with the elevated levels of TILs in Rnf5$^{-/-}$ mice, cytokine analysis identified higher levels of TNF-α and IFN-β in the sera of naïve Rnf5$^{-/-}$ mice (FIG. 3D);

however, these mice exhibited reduced levels of TNF-α, IL-6, IL-17, and IL-1α compared with WT mice after tumor cell inoculation (FIG. 3E). These findings are consistent with reports that high IL-6, TNF-α and IL-17 levels are associated with poor clinical outcome, while lower IL1-α levels are associated with attenuated tumor growth. These findings further support the role of intrinsic inflammation in the anti-tumor response seen in the Rnf5$^{-/-}$ mice.

Figure 3F:
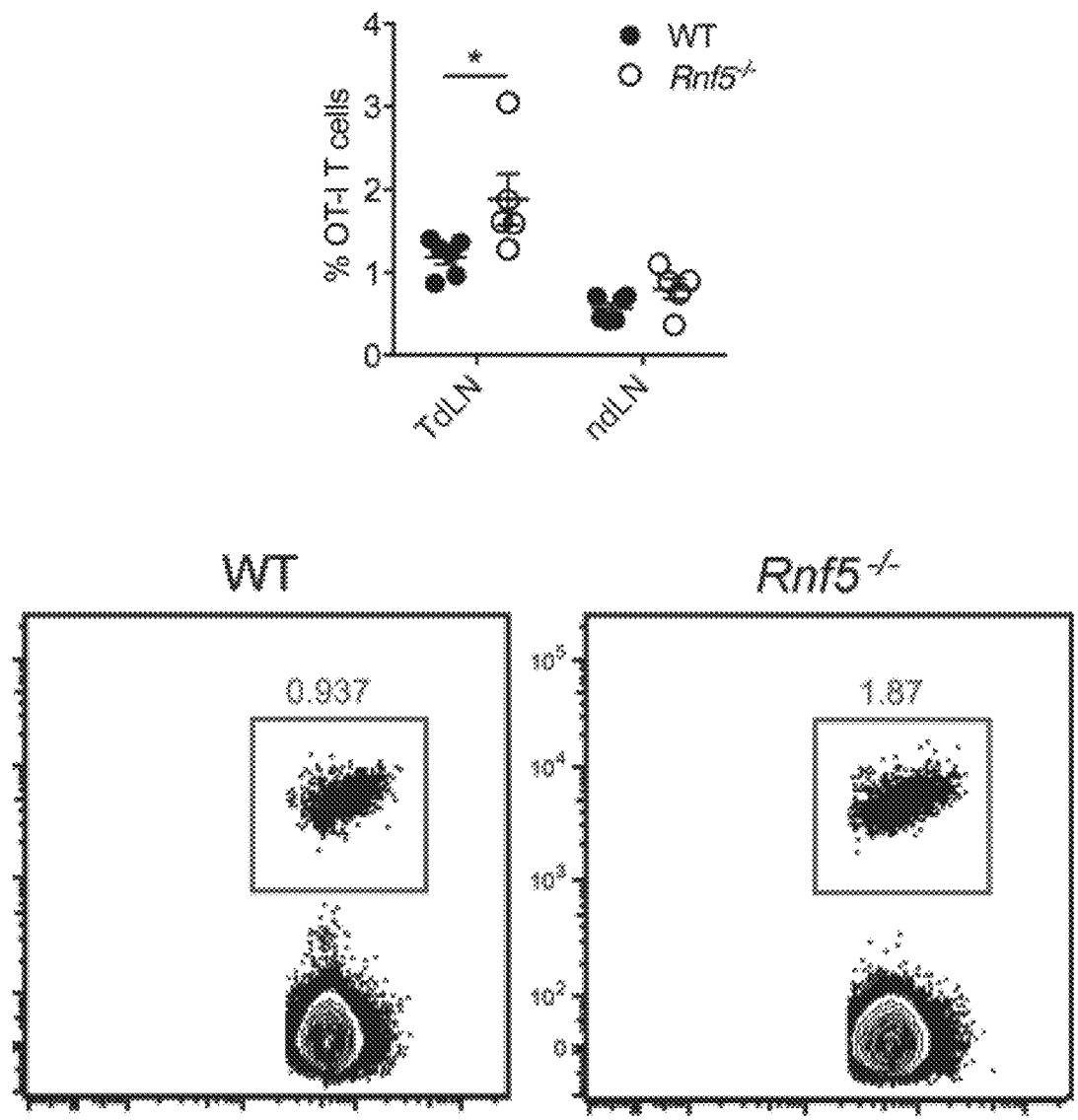

To provide independent support for the role of tumor specific T cells in the anti-tumor response of Rnf5$^{-/-}$ mice, OVA-specific OT-I transgenic CD8$^+$ T cells were transferred into WT or Rnf5$^{-/-}$ recipient mice, and then injected the animals subcutaneously with OVA-expressing B16F10 melanoma cells. Analysis of tumor draining and non-draining lymph nodes showed that OT-I CD8$^+$ T cells were more abundant in the tumor draining lymph nodes of Rnf5$^{-/-}$ mice compared with WT mice, despite their comparable proliferation, whereas no differences were observed in the non-draining lymph nodes (FIG. 3F).

To understand the mechanism by which altered function of Rnf5$^{-/-}$ mice might influence the anti-tumor immune response, changes in the intestinal epithelial cells (IECs) were examined, which cells play critical roles in both innate and adaptive immunity. A significant decrease in the villi length and increase in the depth of crypts was observed in tumor-bearing Rnf5$^{-/-}$ mice, compared with WT mice (FIG. 3C), both of which are associated with increased inflammation, which was reflected in the production of a number of inflammatory cytokines (FIG. 3E). Notably, co-housing of Rnf5$^{-/-}$ and WT mice partially restored villi length to that seen in Rnf5$^{-/-}$ alone animals, suggesting a direct link between the gut microbiota and intestinal structure. IECs from the Rnf5$^{-/-}$ mice exhibited increased expression of ER stress marker BIP (FIG. 3A), which was expected given the role of RNF5 in ER associated degradation. Furthermore, co-housed Rnf5$^{-/-}$ and WT mice partially restored BIP expression to that seen in Rnf5$^{-/-}$ alone mice. Consistent with this, organoids prepared from the IEC of tumor-bearing Rnf5$^{-/-}$ mice also exhibited a higher level of ER stress, increased apoptosis, and were fewer in number than WT IEC-derived organoids. These data point to a possible role of ER stress in key phenotypes seen in the Rnf5$^{-/-}$ mice, which were previously linked with altered immune response. However, treatment of Rnf5$^{-/-}$ mice with the chemical chaperone 4-phenylbutyrate to alleviate ER stress did not affect tumor growth, probably due to its known antagonistic effect on immune cell function.

It was next investigated whether the intestinal alterations in Rnf5$^{-/-}$ mice affect immune cell recruitment and activity. Indeed, a significant increase in CD11c$^+$ DCs was detected in the intestine of Rnf5$^{-/-}$ mice, compared with the WT mice. This finding is consistent with reports that CD11c$^+$ DCs play a role in triggering immune responses that enhance immune checkpoint therapy. Although no difference in DC populations was observed in intestine-proximal lymphoid organs (Peyer's patches) in naïve WT and Rnf5$^{-/-}$ mice, DCs and pDC were significantly more abundant in Peyer's patches from tumor bearing Rnf5$^{-/-}$ mice, than the control WT littermates. These data demonstrate that Rnf5$^{-/-}$ controls dynamic changes in Peyer's patches-associated DCs, which are known to play key roles in the regulation of the immune response.

To probe these findings further, DCs from were isolated Peyer's patches of naïve WT and Rnf5$^{-/-}$ mice and examined their in vitro response to several TLR agonists. Of note, DCs from Rnf5$^{-/-}$ mice produced higher levels of IL-1β in response to TLR7 stimulation, higher levels of IL-1β, IL-17A and IL-27 in response to TLR9 stimulation, and lower levels of IL-10 in response to both TLR7 and TLR9 stimulation, compared with WT DCs. Likewise, production of chemokines, including CCLS, CCL22, CXCL1, and CXCL5 was more effectively induced by TLR7 stimulation of Rnf5$^{-/-}$ DCs compared to WT DCs. The responses of Peyer's patch-derived DCs to TLR7 and TLR9 agonists are consistent with their expression in select organs/tissues.

Example 4A: Anti-Tumor Effects of Mucin and Inulin Administration

Figures 4A, 4B:
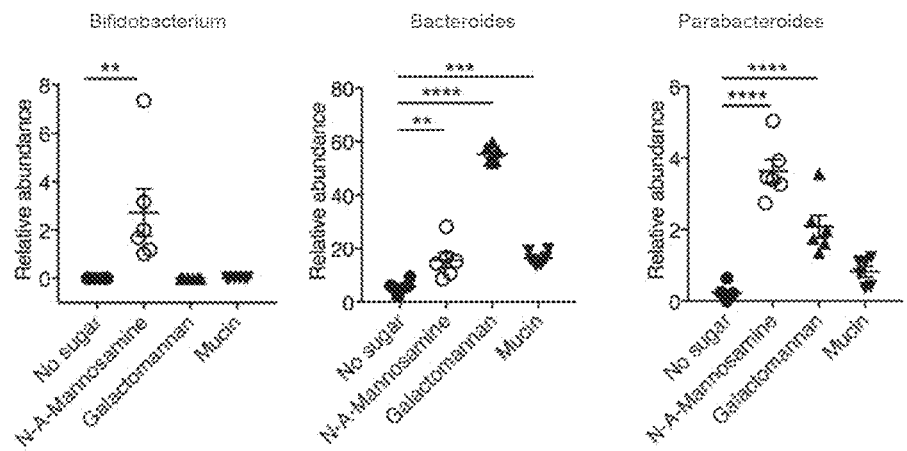

The differences in the gut microbiota of Rnf5$^{-/-}$ and WT mice before and during tumor formation highlighted a functionally coherent group of species that define a food web enriched for species encoding extensive glycosyl hydrolase activities. Similar alterations in the relative abundance of *Bifidobacterium*, *Bacteroides*, *Parabacteroides* were also observed upon cultivation of human fecal samples in media featuring porcine gastric mucin, galactomannans and N-acetyl mannosamine as the sole carbohydrate source (FIG. 4A). These observations implied that altered availability of simple sugar moieties derived from complex carbohydrates may be a key feature of the Rnf5$^{-/-}$ phenotype. Consistent with this notion is the shift in relative abundance of fermentative species, including a reduction in members of *Lachnospiraceae* (*Oribacterium* spp., *Oscillispira*) and *Ruminococcaceae*, that is coupled with increased abundance of species that may cross-feed on available sugars more effectively (i.e. *Bacteroides* spp., *P. merdae*, *P. canis*, *R. microfusus* and *Flavobacterium*). To further assess this possibility, a metabolic model for the gut microbiota was constructed using 11 gut microbiota species that exhibit significant differences in WT and Rnf5$^{-/-}$ mice prior to and following tumor inoculation (FIG. 4B). This analysis allowed the prediction of a defined media capable of sustaining the observed abundance differences over time. In this media, galactose, N-acetyl-D-glucosamine and N-acetyl-D-mannosamine that are components of mucin and glucose-1-phosphate and D-fructose, which are products of inulin catabolism, are predicted to be consumed at a higher rate in Rnf5$^{-/-}$ microbiota, pointing to the possible importance of these substrates in accounting for the observed differences in the gut community (FIG. 4C). These findings, together with the elevated Mucin 2 expression in Rnf5$^{-/-}$ mice, suggested that mucin and/or inulin metabolism may drive the observed anti-tumor phenotypes.

The anti-tumor efficacy of mucin and inulin (see below), together with the strong conservation in taxa dynamics observed in the Rnf5$^{-/-}$ gut microbiota suggests that a key functional distinction between WT and Rnf5$^{-/-}$ microbiota also involves differential glycan and sugar metabolism. Both mucin and inulin suppressed large portions of *Lactobacillus* spp., *Ruminococaceae* and *Lachnospiriaceae* highlighting major shifts in carbohydrate metabolism. The induction patterns of mucin and inulin fed WT and Rnf5$^{-/-}$ mice revealed an enrichment of *Bacteroides* spp., *P. goldsteinii*, *P. merdae*, *P. canis*, *P. koreensis*, unclassified *Pedobacter* and *O. sinus* and reduced abundance for *S. hydroxybenzoicus*, *Blautia* spp. and *J. ignava*. These patterns are highly concordant with those observed in Rnf5$^{-/-}$ microbiota. Spearman and Pearson correlation analysis confirmed that the relative abundance of *B. acidifaciens*, *B. xylanisolvens*, *P. merdae*, *Flavobacterium* correlated with reduced tumor growth and anti-tumorigenic TILs (Table 1). Taken together, the analysis strongly supports that altered metabolism of complex carbohydrates acts as a driver of gut microbiotaelicited changes seen in the Rnf5$^{-/-}$ mice. Complex carbohydrates can be depolymerized in the endosomes of APCs that are then presented to CD4$^+$ T cells by MHC-II molecules.

TABLE 1

Correlation between relative bacterial abundance and tumor growth

| Taxon | Tumorigenic |
|---|---|
| *Bacteroides acidifaciens* | anti |
| *Bacteroides xylanisolvens* | anti |
| *Butyricimonas synergistica* | pro |
| *Butyricimonas virosa* | pro |
| *Dysgonomonas wimpennyi* | anti |
| *Parabacteroides goldsteinii* | pro |
| *Parabacteroides merdae* | anti |
| *Rikenella microfusus* | mixed |
| *Flavobacterium* | anti |
| *Olivibacter* | mixed |
| *Parapedobacter koreensis* | pro |
| *Pedobacter* | pro |
| *Staphylococcus* | anti |
| *Staphylococcus sciuri* | anti |
| *Staphylococcus xylosus* | anti |
| *Alkaliphilus crotonatoxidans* | pro |
| *Alkaliphilus peptidifermentans* | pro |
| *Clostridium taeniosporum* | neutral |
| *Sedimentibacter hydroxybenzoicus* | pro |
| *Blautia coccoides* | pro |
| *Blautia hansenii* | mixed |
| *Blautia wexlerae* | neutral |
| *Johnsonella ignava* | pro |
| *Lachnospira pectinoschiza* | neutral |
| *Moryella indoligenes* | neutral |
| *Oribacterium sinus* | mixed |
| *Ruminococcus gnavus* | pro |
| *Oscillospira* | pro |
| *Oscillospira eae* | pro |
| *Ruminococcus* | pro |
| *Slackia* | pro |
| *Helicobacter ganmani* | anti |
| *Helicobacter hepaticus* | anti |
| *Enterobacter hormaechei* | anti |
| *Ureaplasma* | mixed |

Example 4B: Anti-Tumor Effects of Mucin and Inulin Administration

Mucin2 is prominently expressed by goblet cells and subsequently becomes heavily O-glycosylated where it plays a critical role in intestinal epithelial barrier function, but also serves as a continuous energy source for mucosal-associated bacterial populations. Mucin2 expression was found to be significantly higher in the jejunum, ileum, and colon of tumor-bearing Rnf5$^{-/-}$ mice compared with WT mice (FIG. 3B), but not in the naïve mice.

Furthermore, possible differences were examined in the sugar composition of mucin2, that may influence the antigenicity of mucin2. Analysis of mucin prepared from the small intestine of tumor-bearing Rnf5$^{-/-}$ mice showed higher Galactose, N-acetylgalactosamine (GalNAC), N-acetylglucosamine (GlcNAC) and reduced sialic acid (N-acetylneuraminic acid, Neu5A) compared to WT littermates. Consistent with these findings, GalNAc glycosylation has been implicated in enhanced antigen uptake by DCs and CD4$^+$ T-cell, enhancing humoral responses. Likewise, O-GlcNAc modification was implicated in productive T-cell activation and Neu5Ac was associated with IL-6 and IL-8 expression and tumor promotion. Indeed, lower IL-6 was detected in the serum of tumor-bearing Rnf5$^{-/-}$ mice, compared with WT littermates (FIG. 3E). Moreover, higher Fucose and GalNAc levels were observed in the small intestine and colon of naïve Rnf5$^{-/-}$ mice, compared with the WT littermates. Microbiota-induced host-derived fucose signaling has been implicated in pathogenic intestinal colonization further supporting mucin glycosylation in microbial ecology. Indeed, mucin glycosylation correlates with distinct microbial communities. Consistent with these reports, our findings of altered mucin2 glycosylation, expression and the recruitment of CD11c$^+$ DC in the intestine and the Peyer's patches, is likely to provide the basis for changes observed in tumors and in draining lymph nodes of the tumor bearing Rnf5$^{-/-}$ mice.

To determine whether differences in mucin2 glycosylation might drive the observed differences in the gut microbiota of Rnf5$^{-/-}$ mice, a computer simulation was performed to identify the media requirements (diet) required to maintain the observed abundances of taxa distinguishing Rnf5$^{-/-}$ and WT microbiota in tumor bearing mice. Using a metabolic model, microbial were generated communities using five select species to represent the families that distinguish Rnf5$^{-/-}$ and WT microbiota (Table 2) to model the uptake and utilization of substrates by the communities. The results of the simulation identified substantial differences in the uptake of mucin components including: D-mannose, N-acetyl-D-glucosamine and galactose (Table 3). Using a "leave one out" approach it was determined that the utilization of these products within the model were dependent on the presence of *C. leptum* and *B. longum*, but not of the other community members. These findings suggested that mucin metabolism by Rnf5$^{-/-}$ gut microbiota may be a driver of the anti-tumor phenotype.

TABLE 2

| Bacterial representative | Taxon ID | WT mice with tumor (%) | Rnf5$^{-/-}$ mice with tumor (%) |
|---|---|---|---|
| *Alistipes finegoldii* DSM 17242 | 679935 | 5.7500171803 | 4.44E−004 |
| *Bifidobacterium longum* subsp. *longum* 35B | 1161904 | 0.1151376874 | 8.7056441505 |
| *Clostridium leptum* DSM 753 | 428125 | 10.8539539089 | 78.1451307687 |
| *Barnesiella intestinihominis* YIT 11860 | 742726 | 27.3823153326 | 12.3356251444 |
| *Anaerophaga thermohalophila* DSM 12881 | 886379 | 55.8985758908 | 0.8131555588 |

TABLE 3

| Metabolite name | Formula | WT mice with tumor uptake | Rnf5$^{-/-}$ mice with tumor uptake |
|---|---|---|---|
| D-Mannose | C6H12O6 | 9.4211594308 | 611.8734101881 |
| N-Acetyl-D-glucosamine | C8H15NO6 | 5.9728023201 | 92.6966735483 |
| Galactose | C6H12O6 | 605.9866908433 | 1510.2338975861 |
| Sum | | 621.380652594 | 2214.8039813226 |

Figure 4D:
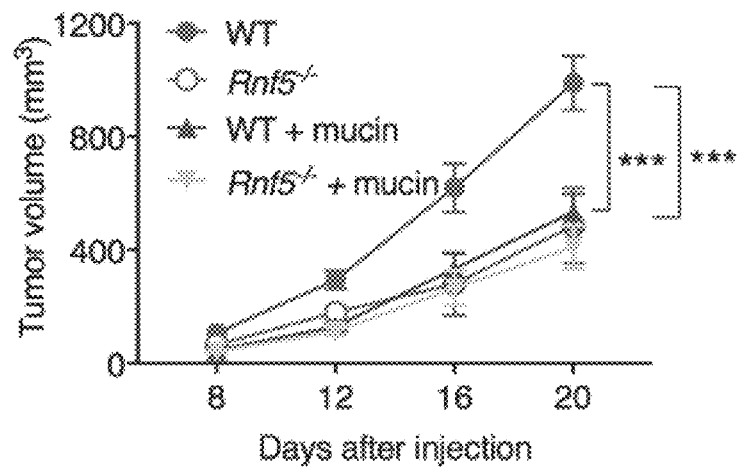
Figure 4E:
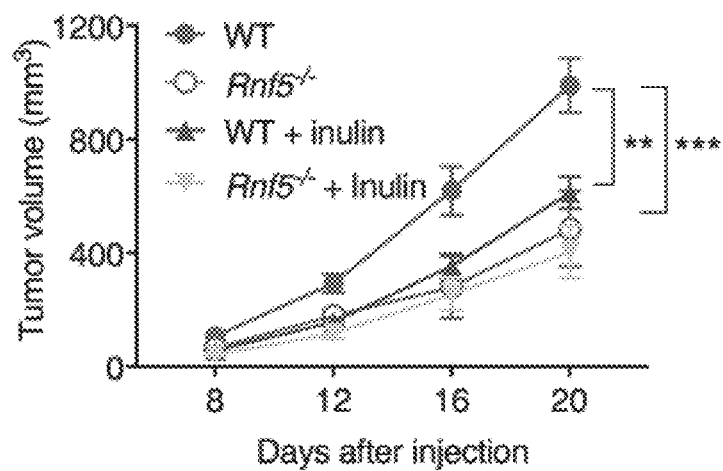
Figure 4F:
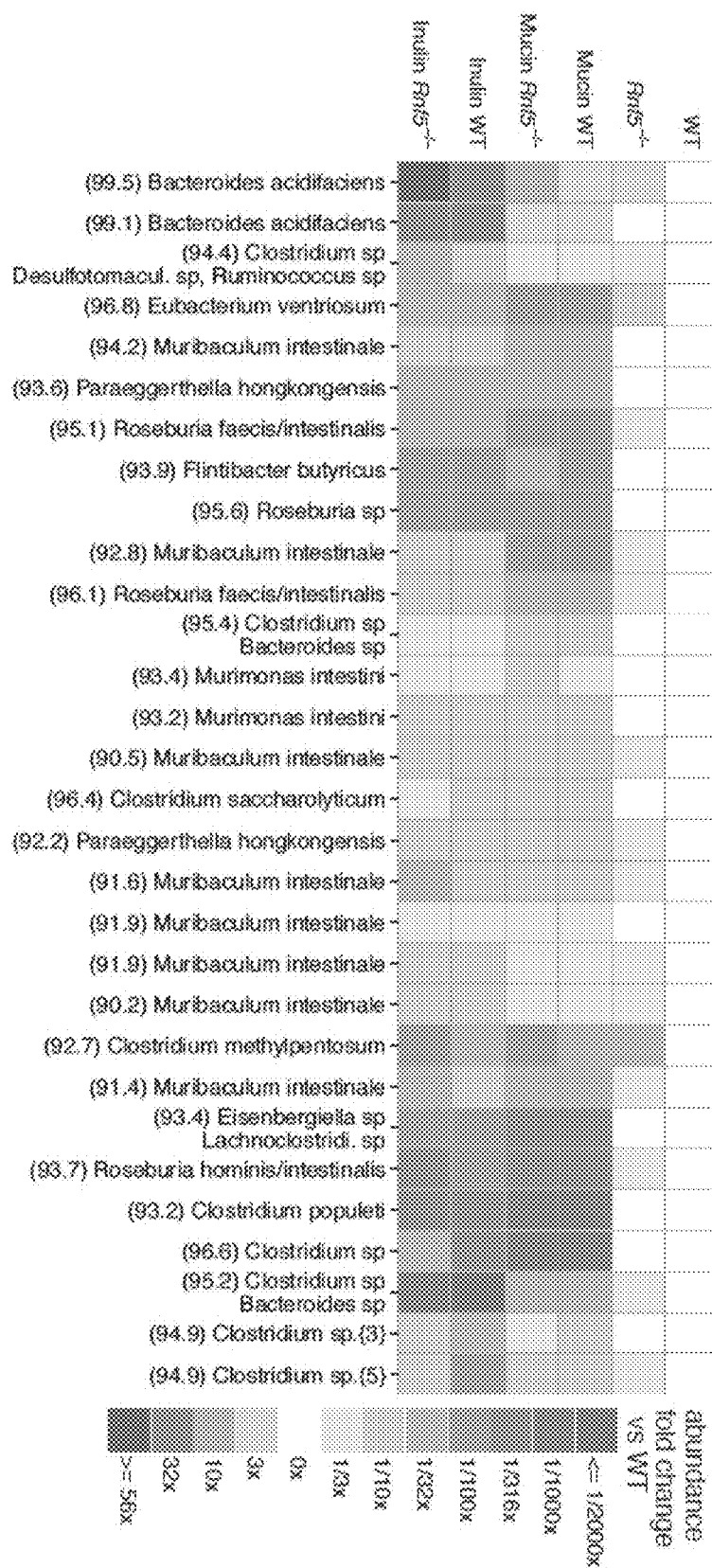

To test this directly it was investigated whether administration of mucin to WT mice could phenocopy Rnf5$^{-/-}$ mice, in terms of tumor growth, immune response and gut microbiota composition. Strikingly, administration of porcine gastric mucin (3% in drinking water) to WT mice attenuated melanoma growth to the degree seen in Rnf5$^{-/-}$ mice, but did not further attenuate tumor growth in Rnf5$^{-/-}$ mice (FIG. 4D). Fecal cultivation experiments in vitro indicated that inulin as the sole carbohydrate source generated communities similar to that of gastric mucin, prompting us to test this prebiotic also in mice in vivo (SNP, unpublished results). Inulin fed mice (15% chow) also exhibited effective inhibition of melanoma growth (FIG. 4E). This prompted us to use machine learning to identify phylotypes that best distinguished WT (non-attenuated tumor growth) from Rnf5$^{-/-}$ and WT mice treated with mucin or inulin (attenuated tumor growth). This resulted in the identification of 30 phylotypes exhibiting consistent alterations in all tumor attenuated phenotypes (FIG. 4F). The immune status of mucin and inulin-fed WT mice also shifted to resemble that of Rnf5$^{-/-}$ mice. Thus, mucin administration increased the number of CD44$^{hi}$CD4$^+$, CD44$^{hi}$CD8$^+$ and CD45$^+$ cells, enhanced TIL cytokine production, increased the number of tumor-associated total DCs and DC subsets. Inulin administration resulted in a similar tumor infiltrating immune cell phenotype. Notably, mucin and inulin also induced a shift in the transcription of immune-related genes to that seen in Rnf5$^{-/-}$ mice, albeit to a lower extent. Collectively, these data suggest that mucin catabolism or inulin/mucin treatment shapes the immune regulatory components of the anti-tumor response.

Figure 6A:
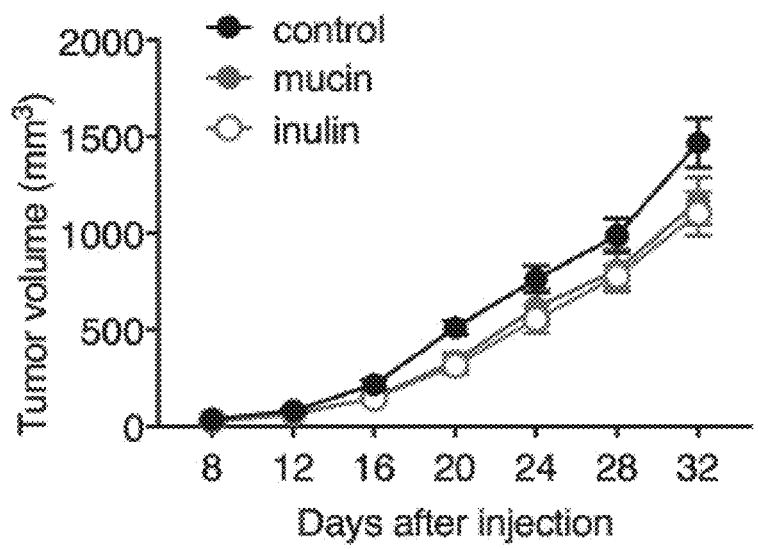
FIGS. 6A-6C demonstrate that prebiotics reduce colon cancer growth, attenuate intrinsic resistance of melanoma to MEKi, and require TLR4 for melanoma growth inhibition.

To determine whether TLR4, the receptor for bacterial lipopolysaccharides, might be involved in the mucin-induced anti-tumor immune phenotype, the growth of mouse melanoma SW1 cells was examined in Tlr4$^{-/-}$ C3H/HeJ mice. Importantly, feeding of mucin or inulin to these mice failed to significantly attenuate melanoma growth (FIG. 6A), demonstrating a requirement for TLR4 in the mucin-induced anti-tumor response. Interestingly, mucin, but not inulin induced an increase in CD8$^+$ T cells and TNF-α-producing tumor-infiltrating CD4$^+$ T cells in these mice, indicating that these cells alone are insufficient to induce tumor regression.

Figure 6B:
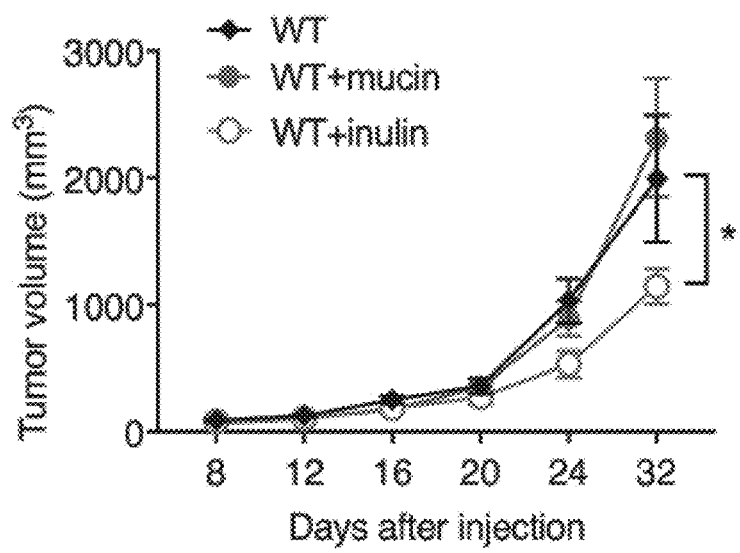
Figure 6C:
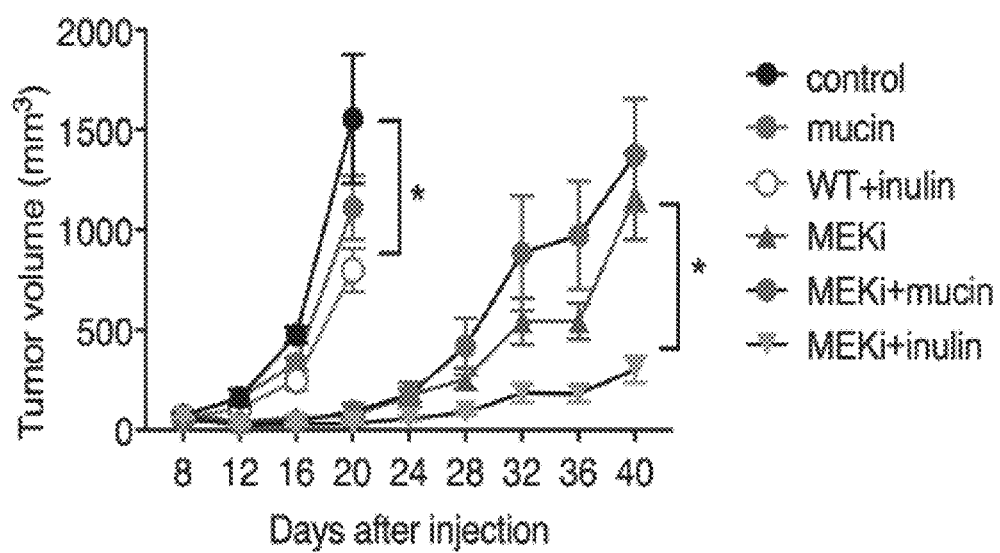

Next, it was determined whether mucin or inulin are also able to impact growth of colon cancer cells, representative of a different tumor type. Growth of MC-38 cells injected to WT mice was attenuated by inulin but not mucin (FIG. 6B). Further, increase in the infiltration of MHC-I and MHC-I on DC cells was noted following inulin administration. Significantly, intrinsic resistance of N-Ras mutant melanoma cells to MEK inhibitor (MEKi) was attenuated upon combined administration of inulin and MEKi (FIG. 6C). Corresponding increase in CD4, CD8, CD45 and DC, including pDC and mDC and MHC-I expression on DC, was identified in tumors subjected to the MEKi+inulin treatment.

Example 5: Anti-CTLA-4 treatment of WT and Rnf5$^{-/-}$ mice

Figure 5:
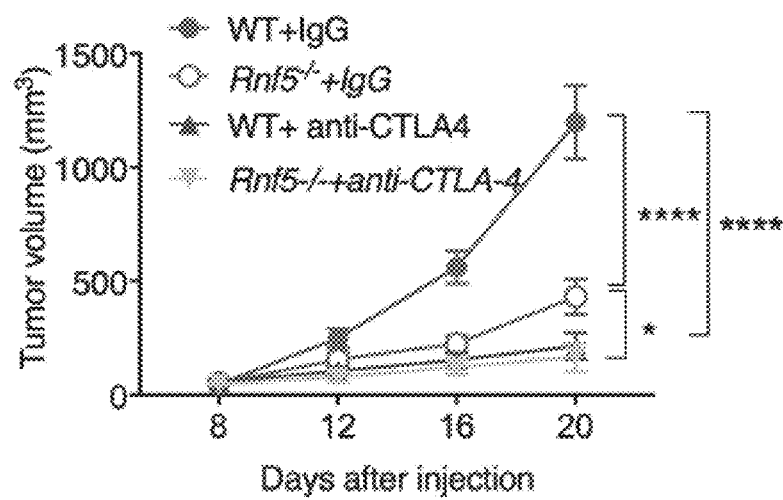
FIG. 5 depicts YUMM1.5 tumor growth in WT or $Rnf5^{-/-}$ mice injected with control IgG or an anti-CTLA-4 blocking GoInVivo antibody (BioLegend) on days 7, 10, 13, and 16 after tumor inoculation (n=9).

Administration of an anti-CTLA-4 blocking antibody reduced melanoma growth in WT mice to the degree seen in Rnf5$^{-/-}$ mice and had a slightly additive effect on tumor growth inhibition in Rnf5$^{-/-}$ mice (FIG. 5). Similarly, anti-CTLA-4 treatment of tumor-bearing WT mice also increased the number of tumor-infiltrating CD44$^{hi}$CD4$^+$ and CD8$^+$ T cells and their cytokine production and increased MHC class II expression on DCs. There was limited overlap in gut microbiota composition following anti-CTLA4 treatment, with that seen in the Rnf5$^{-/-}$ mice or following mucin or inulin treatment. This may be attributed to its direct effect on immune checkpoint activity, which eliminates the need to affect upstream components, such as altering the microbiota which in turn impacts the immune system.

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of treating colon cancer or melanoma in a human subject in need thereof, the method comprising administering to the human subject a composition comprising a therapeutically effective amount of one or more bacteria selected from the group consisting of
    Bacteroides acidifaciens, Bacteroides xylanisolvens, Parabacteroides merdae, and Flavobacterium; and
    administering one or more anti-cancer agents, wherein the one or more anti-cancer agents comprises a Serine/threonine-protein kinase B-raf (BRAF) inhibitor or a Mitogen-activated protein kinase kinase (MEK) inhibitor.

2. A method of treating colon cancer or melanoma in a human subject in need thereof, the method comprising administering to the human subject in combination:
    a therapeutically effective amount of one or more bacteria selected from the group consisting of Bacteroides acidifaciens, Bacteroides xylanisolvens, Parabacteroides merdae, and Flavobacterium; and
    a therapeutically effective amount of mucin or inulin.

3. The method of claim 2, further comprising administering to the human subject one or more anti-cancer agents.

4. The method of claim 3, wherein the one or more anti-cancer agents comprises an immune checkpoint regulator.

5. The method of claim 4, wherein the immune checkpoint regulator is a checkpoint activator or a checkpoint inhibitor.

6. The method of claim 5, wherein the checkpoint activator is an agonist of costimulation by CD27, CD40, OX40, GITR, CD137, CD28, or ICOS, or wherein the checkpoint inhibitor is an antagonist of PD-1, PD-L1, CTLA-4, A2AR, B7-H3, B7-H4, BTLA, IDO, KIR, LAG3, TIM-3, VISTA, CD160, TIGIT or PSGL-1.

7. The method of claim 6, wherein the checkpoint activator is an agonist antibody that binds to CD27, CD40, OX40, GITR, CD137, CD28, or ICOS, or wherein the checkpoint inhibitor is an antagonist antibody that binds to PD-1, PD-L1, CTLA-4, A2AR, B7-H3, B7-H4, BTLA, IDO, KIR, LAG3, TIM-3, VISTA, CD160, TIGIT or PSGL-1.

8. The method of claim 4, wherein the immune checkpoint regulator is CDX-1127, TGN1412, NKTR-214, MEDI0562, MEDI6469, MEDI6383, JTX-2011, pembrolizumab, nivolumab, ipilimumab, tremelimumab, atezolizumab, MGA271, indoximod, Epacadostat, lirilumab, BMS-986016, MPDL3280A, avelumab, durvalumab, MEDI4736, MEDI4737, TRX518, MK-4166, urelumab, or PF-05082566 .

9. The method of claim 3, wherein the one or more anti-cancer agents comprises a Serine/threonine-protein kinase B-raf (BRAF) inhibitor or a Mitogen-activated protein kinase kinase (MEK) inhibitor.

10. The method of claim 9, wherein the BRAF inhibitor is vemurafenib or dabrafenib, or wherein the MEK inhibitor is trametinib, cobimetinib, binimetinib, selumetinib, PD-325901, CI-1040, or TAK-733, or wherein the BRAF inhibitor is vemurafenib or dabrafenib and the MEK inhibitor is trametinib, cobimetinib, binimetinib, selumetinib, PD-325901, CI-1040, or TAK-733.

11. The method of claim 3, wherein the one or more anti-cancer agents comprises a BRAF inhibitor.

12. The method of claim 9, wherein the human subject is identified as having a mutation in the BRAF gene or the Neuroblastoma RAS (NRAS) gene prior to treatment.

13. The method of claim 12, where wherein the human subject is identified as having the V600E, R461I, I462S, G463E, G463V, G465A, G465E, G465V, G468A, G468E, N580S, E585K, D593V, F594L, G595R, L596V, T598I, V599D, V599E, V599K, V599R, V600K, and/or A727V mutation in the BRAF gene prior to treatment.

14. The method of claim 3, wherein the human subject is identified as having poor responsiveness to treatment with the anti-cancer agent prior to initiating administration of the one or more bacteria and/or the one or more prebiotics.

15. The method of claim 2, further comprising evaluating the gut microbiome of the human subject prior to the initiation of treatment.

* * * * *